United States Patent [19]
Song et al.

[11] Patent Number: 5,965,727
[45] Date of Patent: Oct. 12, 1999

[54] FOR SELECTABLE MARKERS AND PROMOTERS FOR PLANT TISSUE CULTURE TRANSFORMATION

[75] Inventors: Hee-Sook Song; Jeffrey E. Brotherton, both of Urbana; Jack M. Widholm, Champaign, all of Ill.

[73] Assignee: Board of Trustees of the University of Illinois, Urbana, Ill.

[21] Appl. No.: 09/001,826

[22] Filed: Dec. 31, 1997

Related U.S. Application Data

[63] Continuation-in-part of application No. 08/937,739, Jul. 25, 1997.
[60] Provisional application No. 60/025,140, Jul. 26, 1996.
[51] Int. Cl.$^6$ ............................ C12N 15/29; C12N 5/04; C12N 15/82; A01H 4/00
[52] U.S. Cl. ........................ 536/24.1; 536/24.1; 800/278
[58] Field of Search ........................... 536/24.1; 800/205, 800/DIG. 40

[56] References Cited

U.S. PATENT DOCUMENTS

| | | |
|---|---|---|
| 4,642,411 | 2/1987 | Hibberd et al. . |
| 4,886,753 | 12/1989 | Marcker et al. . |
| 5,034,322 | 7/1991 | Rogers et al. . |
| 5,290,924 | 3/1994 | Last et al. . |
| 5,352,605 | 10/1994 | Fraley et al. . |
| 5,442,052 | 8/1995 | Bird et al. . |
| 5,466,785 | 11/1995 | De Framond . |
| 5,474,929 | 12/1995 | Pelcher . |

FOREIGN PATENT DOCUMENTS

WO 97/26366  7/1997  WIPO .

OTHER PUBLICATIONS

Taylor. 1997. March issue. The Plant Cell. vol. 9: 273–275).
Napoli et al. The Plant Cell. 1989. vol: 2: 278–289.
Brotherton et al. Planta. 1986. vol:168:214–221.
Bohlmann, J., et al., "Purification and cDNA cloning of anthranilate synthase from *Ruta graveolens*: modes of expression and properties of native and recombinant enzymes", *Plant J.*, 7(3):491–501 (1995).
Bohlmann, J., et al., "Anthranilate Synthase from *Ruta graveolens*", *Plant Physiol.*, 111:507–514 (1996).
Brotherton, J. E., et al., "Anthranilate synthase forms in plants and cultured cells of *Nicotiana tabacum* L.", *Planta*, 168:214–221 (1986).
Carlson J. E., et al., "Separation of Two Forms of Anthranilate Synthetase from 5–Methyltryptophan–Susceptible and –Resistant Cultured *Solanum tuberosum* Cells", *Physiol. Plant.* 44:251–255 (1978).
Froissard, D. et al., "Structural organization of str 246C and str 246N, plant defense–related genes from *Nicotiana tabacum*", *Plant Mol. Biol.* 26(1):515–521 (1994).
Kang, K. K., et al., "selection and Characterization of a 5–Methyltryptophan Resistant Mutant in *Zea mays* L.", *Euphytica*, 69:95–101 (1993).

Kreps, J. A., et al., "Molecular Basis of β–Methyltryptophan Resistance in amt–1, a Mutant of *Arabidopsis thaliana* with Altered Tryptophan Metabolism",*Plant Physiol.*, 110:1159–1165 (1996).
Kreps et al., "Isolation and Characterization of a Mutant of *Arabidopsis thaliana* Resistant to β–Methyltryptophan", *Plant Physiol*, 99:269–275 (1992).
Lee, H. Y., et al., "Selection and Characterization of a Rice Mutant Resistant to 5–Methyltryptophan", *Theor Appl Genet*, 82:405–408 (1991).
Li, J., et al., "The *Arabidopsis thaliana* trp5 Mutant Has a Feedback–Resistant Anthranilate Synthase and Elevated Soluble Tryptophan", *Plant Physiol.*, 110:51–59 (1996).
Niyogi, K. K., et al., "Two Anthranilate Synthase Genes in Arabidopsis: Defense–Related Regulation of the Tryptophan Pathway", *Plant Cell*, 4:721–733 (1992).
Ranch, J.P., et al., "Expression of 5–Methyltryptophan Resistance in Plants Regenerated from Resistant Cell Lines of *Datura innoxia*", *Plant Physiol.*, 71:136–140 (1983).
Shillito, R. D. et al., "High Efficiency Direct Gene Transfer to Plants", Bio/Tech., 3: 1099–1103 (1985).
Singh, B. K., et al., "Shikimate Pathway: Why Does It Mean So Much to So Many", *Oxford Surveys of Plant Molecular of Cell Biology*, 7: 143–185 (1991).
Sasse F. et al., "Site of Action of Growth Inhibitory Tryptophan Analogues in *Catharanthus roseus* Cell Suspension Cultures", Z. Naturforsch, 38c:910–915 (1983).
Sato, S. et al., "Molecular Cloning and the Nucleotide Sequence of the *Clostridium thermocellum* trpE Gene", *J. Biochem*. 105: 362–366 (1989).
Scott et al., "Characterization of a 5–Methyltryptophan Resistant Strain of *Catharanthus Roseus* Cultured Cells", *Phytochemistry*, 18: 795–798 (1979).
Song, H.–S., et al., "Cloning and Characterization of *Nicotiana tabacum* Anthranilate Synthase Genes", Plant Physiology Meeting, Jul. 27–Aug. 2, Abstract 534, *Plant Physiol.*, 111 S: 125 (1996).
Song, H.–S., et al., "Session 19, Gene Structure/Characterization", Plant Physiology Meeting, Aug. 2–6, Abstract 128, *Plant Physiol.*, 114 S: 43 (1997).

(List continued on next page.)

*Primary Examiner*—Douglas W. Robinson
*Assistant Examiner*—Ousama M-Faiz Zaghmout
*Attorney, Agent, or Firm*—Wean Khing Wong; Applegate Valauskas Rosen & Bernstein

[57] ABSTRACT

A selectable marker, the ASA2 gene of Nicotiana tabacum, is provided for transforming plant cells. The ASA2 promoter sequence is also provided which is capable of directing tissue culture specific transcription of a downstream structural gene. Also disclosed are truncated forms of the ASA2 promoter which are capable of directing high level constitutive transcription of downstream structural genes. Constructs containing the above genes and promoters are also disclosed.

11 Claims, 21 Drawing Sheets

OTHER PUBLICATIONS

Stewart, Jr., C. N. et al., "Genetic Transformation, Recovery, and Characterization of Fertile Soybean Transgenic for a Synthetic *Bacillus thuringiensis* cyrlAc Gene", *Plant Physiol.*, 112: 121–129 (1996).

Tam et al., "Selection and Characterization of β–Methyl-tryptophan–Resistant Lines of *Lemna gibba* Showing a Rapid Rate of Indole–3–Acetic Acid Turnover", *Plant Physiol*, 107: 77–85 (1995).

Vain, P., et al, "Development of the Particle Flow Gun", *Plant Cell, Tissue, & Organ*, 33:237–246 (1993).

Vermeulen et al., "Agrobacterium mediated transfer of a mutant Arabidopsis acetolactate synthase gene confers resistance to chlorsulfuran in chicory (*Cichorium intylbus* L.)", *Plant Cell Reports*, 11: 243–247 (1992).

Wakasa, K. et al., "V. 2 Rice Mutants Resistant to Amino Acids and Amino Acid Analogs", in *Biotechnology in Agriculture and Forestry*, vol. 14 Rice, Y.P.S. Bajaj ed. (Springer–Verlag, New York, 304–315, 1991).

Widholm, J.M., "Tryptophan Biosynthesis in *Nicotiana tabacum* and *Daucus carota* Cell Culture, Site of Action of Inhibitory Tryptophan Analogs", *Biochimica et Biophysica Acta*, 261: 44–51 (1972).

Widholm, J.M., "Anthranilate Synthetase from 5–Methyl-tryptophan–Susceptible and –Resistant Cultured *Daucus carota* Cells", *Biochimica et Biophysica Acta*, 279: 48–57 (1972).

Widholm, J.M., "Cultured *Nicotiana tabacum* Cells with an Altered Anthranilate Synthetase Which is Less Sensitive to Feedback Inhibition", *Biochimica et Biophysica Acta*, 261: 52–58 (1972).

Widholm J.M., "Relation between Auxin Autotrophy and Tryptophan Accumulation in Cultured Plant Cells", *Planta*, 134: 103–108 (1977).

Widholm, J., "Differential Expression of Amino Acid Biosynthetic Control Iso–Enzymes in Plants and Cultured Cells", in *Plant Cell Culture: Results and Perspective*, Sala, F., et al., ed., pp. 157–159 (1980).

Widholm, J. M., "In Vitro Selection with Plant Cell and Tissue Cultures: An Overview", *Iowa State J. Res.*, 62(4):587–597 (1988).

Figure 4A

```
        1                                                              50
TASA1   M------- -------- -------- -------- --------
TASA2   -------- QSLPISYRLF PATHRKVL- -PFAVISSRS STSALALRVR
RASA1   MIT-LNVETP P---LTRSQL PSTFRVSSAA ----SVNFND RVATSRWRPN
RASA2   MSAA--ATSM QSLKFSNRLV PP--SRRLSP VPNNVT--CN NLPKSAAPVR
AASA1   MSSSMNVATM QALTFSRRLL PSVASRYLSS SSVTVTGYSG RSSAYAPSFR
AASA2   MSA-VSISAV KSDFFTVEAI AVTHHRTPHP PHFPSLRFPL SLKSP--PAT
CTRPE   M------- -------- -------- -------- --------

51                                                             100
TASA1   -------- -------- -------- -------- --------
TASA2   TLQCRC--- LH------ -------- -------SS SLVMDEDRFI
RASA1   SLSLTTSS- ---Y--RLRTL KCAASASTSA STSASPSPSP SLVDQSANFH
RASA2   TVKCCASS- ----WNSTING AAATTNGASA ASNGASTTTT TYVSDATRFI
AASA1   SIKCVSVS- ---PEASI--- -------- -------- --VSDTKKLA
AASA2   SLNLVAGSKL LHFSRRLPSI KCSYTPSLDL SE------ ---EQFTKFK
CTRPE   -------- --FYPTLDEV KIM----- -------- --------

101                                    ****    150
TASA1   -------- -------- -------- --DDREAPSF LFESVEPGSQ
TASA2   EASKSGNLIP LHKTIFSDHL TPVLAYRCLV KEDDREAPSF LFESVEPGFR
RASA1   EASKKGNLIP LYRCIFSDHL TPVLAYRCLV KEDDRDAPSF LFESVEPGSQ
RASA2   DSSKRANLVP LYRCIFADHL TPVLAYRCLV QEDDKETPSF LFESVEPG-P
AASA1   DASKSTNLIP IYRCIFSDQL TPVLAYRCLV KEDDREAPSF LFESVEPGSQ
AASA2   KASEKGNLVP LFRCVFSDHL TPILAYRCLV KEDDRDAPSF LFESVEPGSQ
CTRPE   --AKDYNIIP VTMEVYADME TPI-----SLF KRFEESSCCF LLESVEGGEK
                                        **   ** ***** *
```

Figure 4A (continued)

```
        151       *                                                                   200
TASA1   MSSVGRYSVV GAQPAMEIVA KENKVIVMDH NNETMSEEFV EDPMEIPRKI
TASA2   GSSVGRYSVV GAQPSMEIVA KEHNVTILDH HTGKLTQKTV QDPMTIPRSI
RASA1   ASSIGRYSVV GAQPAIEIVA KENMVTILDH EGGQRTEQFV EDPMDVPRRI
RASA2   ISTVGRYSVV GAHPVMEVIA KDNMVTVMDH EKGSLVEEVV DDPMEIPRRI
AASA1   MSSVGRYSVV GAQPAMEIVA KENKVIVMDH NNETMTEEFV EDPMEIPRKI
AASA2   SSNIGRYSVV GAQPTIEIVA KGNVTVMDH GASLRTEEEV DDPMMVPQKI
CTRPE   W---ARYSII GKNPFLVVES YKNKTIIRER NGSQREVE-- GNPVEIIKGI
             ***.::   *   .          .      . :    *            +

201                                                                           250
TASA1   SEKWNPDPQL VQDLPDAFCG GWVGFFSYDT VRYVEKRKLP FSKAPEDDRN
TASA2   SEGWKP--RL IDELPDTFCG GWVGFYFSYDT VRYVENRKLP FLRAPEDDRN
RASA1   MEGWK--PQL IDELPEAFCG GWVGYFSYDT VRYVEKKKLP FFSAPTDDRN
RASA2   SEDWK--PQI IDDLPEAFCG GWVGFFSYDT VRYVEKKKLP FSKAPQDDRN
AASA1   SEKWNPDPQL VQDLPDAFCG GWVGFFSYDT VRYVEKRKLP FSKAPEDDRN
AASA2   MEEWN--PQG IDELPEAFCG GWVGYFSYDT VRYVEKKKLP FSNAPEDDRS
CTRPE   MGKFKGAN-- LPNLPR-FNG GAVGYFGYDL IRHYEN--LP --NVPEDDMG
              :: .**   : **.***.*:  .*   **               *    *

251                                                                           300
TASA1   LPDMHLGLYD DVVVFDHVEK KAYVIHWIRL DGSLPYEKAY SNGMQHLENL
TASA2   LADIQLGLYE DVIVFDHVEK KAHVIHWVQL DQYSSLPEAY LDGKKRLEIL
RASA1   LPDVHLGLYD DVIVFDHVEK KAFVIHWVRL DQYSSVAEAY NDGMNRLENL
RASA2   LADMHLGLYN DVIVFDHVEK KVYVIHWVRL NQQSSEEKAY AEGLEHLERL
AASA1   LPDMHLGLYD DVVVFDHVEK KAYVIHWIRL DGSLPYEKAY SNGMQHLENL
AASA2   LPDVNLGLYD DVIVFDHVEK KAYVIHWVRI DKDRSVEENF REGMNRLESL
CTRPE   LPECHFMFTD EVLVYDHLKQ KIHII--VNL HVNGNIERAY ISAVDRIKTI
        *   :   :    * **::  *  *   :         :                
```

Figure 4B

```
       301
TASA1  VAKLHDIEPP KLAAGNVNLQ TRQFGPSLDN SNVTCEEYKE AVVKAKEHIL
TASA2  VSRVQGIESP RLSPGSVDFC THAFGPSLTK GNMTSEEYKN AVLQAKEHIA
RASA1  VSRVHDIVPP KLRSGSIKLH TRHFGPKLER SSMTSEAYKE AVLEAKEHIL
RASA2  VSRVQDENTP RLAPGSIDLH TGHFGPPLKK SNMTCEEYKM AVLAAKEHIQ
AASA1  VAKLHDIEPP KLAAGNVNLQ TRQFGPSLDN SNVTCEEYKE AVVKAKEHIL
AASA2  TSRIQDQKPP KMPTGFIKLR TQLFGPKLEK STMTSEAYKE AVVEAKEHIL
CTRPE  HREILDTRWK TADNSVLSYN KKKNELAVT- SNISKEDFCR NVLKAKQYIR
       *****.***. .        .         *  .  . *   .**. ***.

351                                                400
TASA1  AGDIFQIVLS QRFERRTFAD PFEVYRALRV VNPSPYMGYL QARGCILVAS
TASA2  AGDIFQIVLS QRFERRTFAD PFEVYRALRI VNPSPYMTYI QARGCILVAS
RASA1  AGDIFQIVLS QRFERRTFAD PFEIYRSLRI VNPSPYMTYL QARGCILVAS
RASA2  AGDIFQIVLS QRFERRTFAD PFEVYRALRV VNPSPYMTYM QARGCVLVAS
AASA1  AGDIFQIVLS QRFERRTFAD PFEVYRALRV VNPSPYMGYL QARGCILVAS
AASA2  AGDIFQIVLS QRFERRTFAD PFEIYRALRI VNPSPYMAYL QVRGCILVAS
CTRPE  DGDIFQVVLS QRLCVETNEN PFNIYRALRV INPSPYMYYL KFGGYRIIGS
       *****.*** **. .  .   ** .**.**. .******.   .  *** .*

401                                                450
TASA1  SPEILTKVKQ NKIVNRPLAG TSKRGKNEVE DKRLEXELLE NEKQSAEHIM
TASA2  SPEILTRVKK RRIVNRPLAG TSRRGKTPDE DVMLEMQMLK DEKQRAEHIM
RASA1  SPEILTRVKK RKITNRPLAG TIRRGKTRKE DLVFEKELLN DEKQCAEHIM
RASA2  SPEILTRVKK NKIVNRPLAG TARRGRTTEE DEMLETQLLK DAKQCAEHVM
AASA1  SPEILTKVKQ NKIVNRPLAG TSKRGKNEVE DKRLEKELLE NEKQCAEHIM
AASA2  SPEILLRSKN RKITNRPLAG TVRRGKTPKE DLMLEKELLS DEKQCAEHIM
CTRPE  SPEMLVRVEN GIVETCPIAG TRKRGRTKEE DEALEKELLS DEKEIAEHVM
       ***.* . .  .. . .**  * .* . .*  *  * .* .  . .. ***.*
```

Figure 4B (continued)

```
      451
TASA1 LVELGRNDVG KVTKYGSVKV EKLMNIERYS HVMHISSTVT GELQDGLTCW
TASA2 LVDLGRNDVG KVSKPGSVNV EKLMSVERYS HVMHISSTVS GELLDHLTCW
RASA1 LVDLGRNDVG KVSEPGSVKV EKLMNIEHYS HVMHISSTVT GELLDHLTSW
RASA2 LVDLGRNDVG KVSKSGSVKV EKLMNVERYS HVMHISSTVT GELQDNLSCW
AASA1 LVDLGRNDVG KVTKYGSVKV EKLMNIERYS HVMHISSTVT GELQDGLTCW
AASA2 LVDLGRNDVG KVSKPGSVEV KKLKDIEWFS HVMHISSTVV GELLDHLTSW
CTRPE LVDLGRNDIG RVSKFGTVAV KNLMHIERYS HVMHVTNVQ GEIREDKTPF
      ** .****** .*.   *   .  *     ****  .

501                                                550
TASA1 DVLRAALPVG TVSGAPKVKA MELIDELEPT RRGPYSGGFG GVSFTGDMDI
TASA2 DALRAALPVG TVSGAPKVKA MELIDQLEVA RRGPYSGGFG GISFSGDMDI
RASA1 DALRAALPVG TVSGAPKVKA MEIIDKLEVT RRGPYGGGFG GISFTGDLDI
RASA2 DALRAALPVG TVSGAPKVKA MELIDELEVN RRGPYSGGFG GISFTGDMDI
AASA1 DVLRAALPVG TVSGAPKVKA MELIDELEPT RRGPYSGGFG GVSFTGDMDI
AASA2 DALRAVLPVG TVSGAPKVKA MELIDELEVT RRGPYSGGFG GISFNGDMDI
CTRPE DALMSILPAG TLSGAPKVRA MEIIDELETV KRGPYGGAIG YLSFNGNLDS
      *  *  ** * . ******  **. .* .  .  ***. *.  . **. . .

551                                                600
TASA1 ALSLRTIVFP TACQYNTMYS YKDANKRREW VAYLQAGAGV VADSDPQDEH
TASA2 ALALRTMVFL NGARYDTMYS YTDASKRQEW VAHLQSGAGI VAHSNPDEEQ
RASA1 ALALRTMVFQ TATRYDTMYS YKDVDKRREW IAHLQAGAGI VADSDPADEQ
RASA2 ALALRTIVFQ TGTRYDTMYS YKNATKRRQW VAYLQAGAGI VADSDPDDEH
AASA1 ALSLRTIVFP TACQYNTMYS YKDANKRREW VAYLQAGAGV VADSDPQDEH
AASA2 ALALRTMVFP TNTRYDTLYS YKHPQRRREW IAHIQAGAGI VADSNPDDEH
      * *  ***  *       . **    .   *  *  .    *   **. .  **
```

Figure 4C

```
CTRPE   CITIRTIILK DGKAY----- ---------- ---------- ---VQAGAGI VADSVPEREY
        ..:.**....  *                               .:*.****.  *****.*
                                                                    650
        601
TASA1   CECQNKAAGL ARAIDLAESA FVKKX----- ---------- ---------- ----------
TASA2   IECENKVAGL CRAIDLAESA FVKGRHKPSV KINGSVPNLF SRVQRQTSVM ----------
RASA1   RECENKAAAL ARAIDLAESS FIEK------ ---------- ---------- ----------
RASA2   RECQNKAAGL ARAIDLAESA FVNKSSS--- ---------- ---------- ----------
AASA1   CECQNKAAGL ARAIDLAESA FVKK------ ---------- ---------- ----------
AASA2   RECENKAAAL ARAIDLAESS FLEAPEFTTI TPHINNI--- ---------- ----------
CTRPE   EECYNKAMAL LKAIEEAGEI R--------- ---------- ---------- ----------
        :* :* .*  .*       .:* :.....

651
TASA1   ---------- ----------
TASA2   SKDRVHEKRNX ----------
RASA1   ---------- ----------
RASA2   ---------- ----------
AASA1   ---------- ----------
AASA2   ---------- ----------
CTRPE   ---------- ----------
```

Figure 9

```
-2287  CTAGTTATGG ATGAGGACAG GTTCATTGAA GCTTCAAATC TATTCGATAG
-2237  TGGGACCTAC GTCTCAAATC CCGAAAAAAC TCGCGAAATC CGAACACCCG
-2187  TTCCGCTACG AGTTCAACCA TACAAAAATT ATCCAATTCT GATGTCAACT
-2137  CGACCCTCAA ATCTTCAATT AAAGTCTTTG AAGACTTCTA TCATTTTCAA
-2087  CTCAATCTTT ATCCATTTG  AACTAAACAC TATTTCCATA AAACCTTATT
-2037  GATACGTATA AATAATACTC TTACACCCAA GAATTATACT CTTAATCACC
-1987  CATCATTACC CAAACTCGGA ATTGAAGATT AAAACCTTAC CTCTTTGATG
-1937  AAGAACTTGA GGGATTTTTT TGTTGGATTT CAAGGCTTGG ACAAGAATTT
-1887  GATGAGCAAG ACACTTTATC TACTTCCTCT CTCTAGAACA CTCTCACTTC
-1837  TCTCTAAAAT CATCAGATAG TTGCCCCAAA ACCTATTTAT CAAAATAGAG
-1787  TCGGGTAATG AAAATAGGTA AATGGACCCT CCAAACTCAG GTATGCGATT
-1737  GCACAATGGA TATACGGGTC GCACAATGGA CCACCAAATC GATGCCGAAA
-1687  ACTGGGTTGC GCTGGACAGG TCTGCGACCC ATTTACGGT  CGCACAATGT
-1637  GCTACGAAGA GGAATTCACA TAGATTTAGG AAGGGCCTGT TGTATTTGTG
-1587  TACAAGCTAA AGTTTTTGA  AAAACAAATA CCTTTGGTCA CTTTCATTGT
-1537  CAAATAGGTT TTTCCTTCGT ATACCTTACT TACATCACAT AGTGATTATG
-1487  CGATCGCACA ATTTACCGCA TAATCGTATT TTTCCAGCTT TTGGTAATTT
-1437  AATCATAACT TTTTTATGA  ATATCCAAAT GACGAACTGT TTGAAGCGTT
-1387  AGAAACTAGA CTCAAAGATC TTTCATTTTA TAGGCAATAC GGCACATAAT
-1337  ATTTTGTATC ATGAGAGTTA TTCTCATTTG AAGTTAGGTC TTGTGTGAAC
-1287  TCACTTGAAA CTTTAGTCTT ATGAAATTTC CAACTTCTAC ATCCGATTCC
-1237  GAAACCTATC GAATCAAGTC CGATTGACCT CAAATTTTGC ATACAAGCCA
-1187  TAAATGACAT AACAGAGCTA TAAAATTTTT CGAAACGGGA TTCCGGCTCC
-1137  GATATCAAAA AGTCAACCCT GTGGTCAAAC TTGGAAATCT TTAGCCTTTA
-1087  AATTACTAGT TTCCGTTAAA TGGTCATAAC TTGAGTTATG GACCTCCAAA
-1037  TTAAATTCCG GGCATACGCC CAAGTCCCAT ATCACGATAC GAACCTATAG
-987   GAACTTTCAA AATATTGATC CGGATCCGTT TGCTCAAAAT GTTGATCAAA
-937   GTCAACTCAG TTGAGTTTTA AGGCTCTAGT TCACATTTTA ATCCATTTTC
-887   ACCTAAAAAC TTTCCGGAAA ATTTTACGGA TTTCGCACGC AAGTCGATGA
-837   ATGACTTTTG GAGGTCTTAG AACACGTAAT TAATTATTAA ATTTAAAGAT
-787   GACATTTTGG ATAATCACCC AAGTAGTACA AATTTTTTAT GCGGTGATTA
-737   TATTTGCCAA TCCATCAAGC CAAACATGTC GTAATTAGTC ATAAATTAAG
-687   TTATACAGGA AGAATAATAC GAGAAATATA ATACCTAAAT TAATAAATAC
-637   TACTATAAAA TTATAATATT GATATTGTGG TTGTATTGCC CATTTCATTA
-587   GAAAGGATAT ATGATGTATA ATATAAAATT TTACAATGTT ATTCTTGTTT
-537   TTAAAGTTAA TAAAAATTTA AATATGAAT  TTAAGGTTAT TCTTGTTTAT
-487   AGATTCTTTA TATCATAAAG CTAATCCTCG TATAAATTAT TTCATATTCG
-437   ACTCATATAA ACTAATACTG AAATTACTAT ATAAGATTAT ATACCGGTAT
-387   ATATTGGAAA CGAGACATCA GCCAAATGTG TCCAAAAATA ATAAATATCA
-337   AATTTTATAT CAGGATTATT TTTTTTGATT ATGTTAACAA AGTTAAAAGT
-287   ATCAGACTAT AAATACTGTA GATAAGATCA GCCATTATTA GAGATAATAC
-237   TCTCACTACC TATATTGAAA GTGAAGTAGA CATTTTCTGA GGTGGAATAT
-187   TTAAAACGTT TCAGACATT  TAAAACCTGG AATGCGGAGG CAAAGTAGTG
-137   TAGTACTTAC TAGTAGTATA AATAAGTGAT CCCATTTTCA AAGTCACCGT
-87    CAAAAATCCC CATTTCACCG TTTCCTCGTT TCTCCTCCTC ACTAATTTTG
-37    TCTCTTTCTC TTGGTTTGCT ATTGTGCTCT TGTAGGA    ATG CAGTCGT
                                                  -1
```

Figure 10
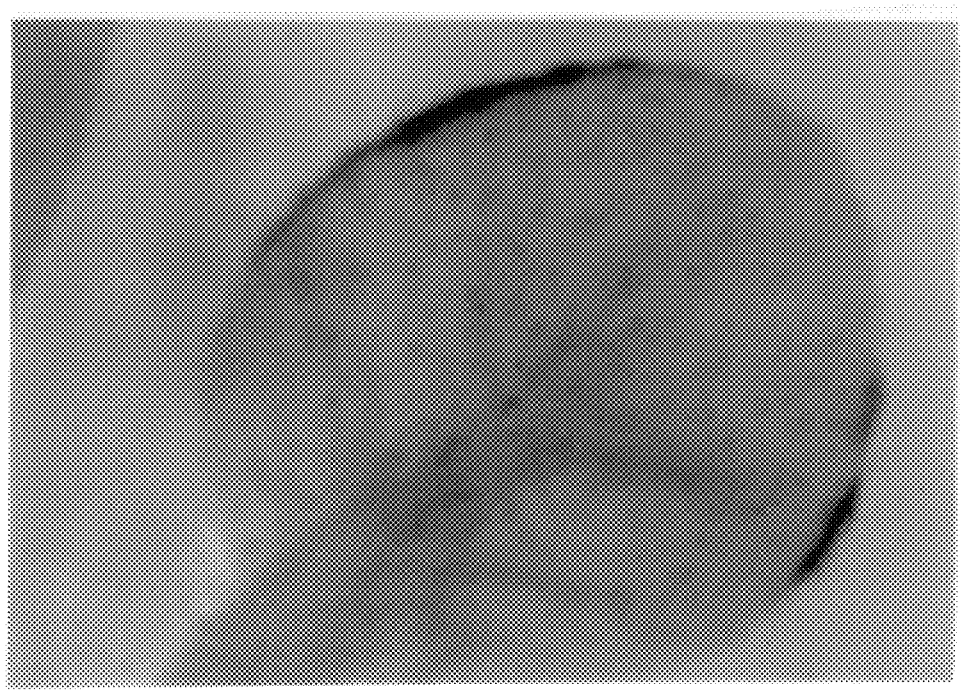

Figure 15A

```
         1                                                              50
ASA2G    AGGACGAAAT GATGTAGGAA AGGTTTATTA CTGACCATTT CAGCATTTTT
ASA3G    AGGACGAAAT GATGTAGGAA AGGTTTATTA CTGACCATTC CAGAATTTTT
         ********** ********** ********** *********  ***  ******
         51                                                             100
ASA2G    GCATCACCAA GAGCTTTGAA ATATATCTGG TTCAATGAGT GGGAGAGAAC
ASA3G    GCATCACCAA GAGCTTTAAT ATATATCTTG TTCAATGAGT GGCAGAGAGC
         ********** *******  * ******* *  ********** **  *****  *
         101                                                            150
ASA2G    CTTGTTTGGT AGAAAATTAG AAATGGAAAT ACTAAAAATA TTAACTGCTT
ASA3G    CTTGCTTGGT AAAAAATTAG AAATAGAAAT ACTAAAATTA TTAACTGCTT
         ****  ***** * ******** ****  ***** ******* ** **********
         151                                                            200
ASA2G    CCTTTTTCCG CCCATCTTTT TCATGAAATG CTAATATAGA GGGTGTCATG
ASA3G    CCTTTTTCTG CCCATTTTTT TCATGAAATG CTAACATAGA GGGTGTCATG
         ********  * *****  **** ********** ****  ***** **********
         201                                                            250
ASA2G    CAGCATGCAT TATCTACTTC TACTACCCTC TTTTACATTC TAGCCATATA
ASA3G    CAGCATGAAT CATCTGCTTC TGCTACACTC TTTAACATTC TAGCCATACA
         *******  ** ****  **** *  ****  *** *** ****** ********  *
         251                                                            300
ASA2G    AAATGCAATG GCC.ACCCCC CTAACCTTTC CTGTTAGTTG TTACCTCTCT
ASA3G    AAATGCAATG TCCGTCCCCC TTATTCTTTC CTGTTAGTTG TTACCTCTCT
         **********  ***  *****  **  ***** ********** **********
         301                                                            350
ASA2G    GCTATCACAG TGTTAGTATC TTCTGTTCCA CGATATACTT CAGGTAGAGC
ASA3G    TCTATGACAG TGTGAGTATC TTCTGTTCCA CAATATACTT CAGGTAGAGC
          ****  ****  ***  ****** **********  * ******* **********
         351                                                            400
ASA2G    CTTTTCCAAC AGTGATAGAA CCCCTAGACG TTGGTTGTTT TATGTAAATA
ASA3G    CCTTTTCAAC TGTGATAGAA CCCCTCGGCG TTGGTTGTTT CATGTAAATA
         *  *** ****  ********** *****  * **  **********  *********
         401                                                            450
ASA2G    CAGCAACTAA ACTTATGGGG TGCCTCTTTT CTTGTTTCCT GAATATGTTT
ASA3G    CAACAACTGA ACTT...GGC TGCCTCTTTT TTTGTTTCCT GAATATGTTT
         **  *****  * ****    **  ********** ********  **********
         451                                                            500
ASA2G    CGACTTGCAC TTGAAAAATA TTTTGGGTTA CCCAACTATT TCCTTTTCTT
ASA3G    TGACTTGCAC TTGAAAAATA CATT.GGTTA CCCAAATATT TCCTTTTCTT
          ********* **********  **  ***** *****  **** **********
         501                                                            550
ASA2G    GCTATAGGTG TCAAAACCTG GTTCTGTGAA TGTCGAAAAG CTCATGAGCG
ASA3G    GCTATAGGTG TCAAAACCTG GCTCTGTGAA TGTTGAAAAG CTCATGAGCG
         ********** **********  * ********  ***  ****** **********
         551                                                            600
ASA2G    TTGAGCGGTA TTCCCATGTG ATGCACATAA GCTCCACGGC GAGTCCATAT
```

Figure 15B

```
ASA3G    TCGAGCGGTA TTCCCATGTG ATGCACATAA GCTCCACGGC GAGTCCATAT
         * ******** ********** ********** ********** **********
         601                                                 650
ASA2G    TTTGATTTCA TCCGAGGTTG TACTGGAATC TTAAATTGCC TTTGATATTC
ASA3G    TTTGATTTCG TCCGAGGTCA TACTGGAATC TAAATTGCCT TTTGATGTTC
         ********* *******    ********** * ** *  *  ****** ***
         651                670
ASA2G    TTGTGGG... ..........
ASA3G    TTTGTTGGCT CTAATTTTCC
         **    *
```

FOR SELECTABLE MARKERS AND PROMOTERS FOR PLANT TISSUE CULTURE TRANSFORMATION

This application is a continuation-in-part of U.S. patent application, Ser. No. 08/937,739, filed on Jul. 25, 1997, which in turn is based on U.S. provisional application Ser. No. 60/025,140 filed on Jul. 26, 1996.

TECHNICAL FIELD OF THE INVENTION

The present invention relates to the field of plant genetics. In particular, the invention provides novel selectable markers and promoters for plants.

BACKGROUND OF THE INVENTION

The selection of mutants using cultured plant cells is in principle similar to that done with microorganisms, but in practice is much more difficult. The reasons for the difficulties include the usual clumpy nature of plant cell cultures; single cells or protoplasts usually cannot be easily grown to form clones, cell growth is slow and the cells are usually not monoploid. Despite these problems a large number of successful selection experiments have been carried out to produce mutants of value for producing compounds, for biochemical and molecular biology studies, for markers in genetic experiments and for improving crop plants. Part of the reason for the success is that cell systems allow the screening of millions of cells for the desired trait.

Whether the selected phenotype is under genetic or epigenetic control can most easily be determined by regenerating plants and by following the phenotype in progeny. Genetically controlled phenotypes would be inherited by progeny and would generally be more stable at the cell level in comparison to epigenetically controlled traits. A large number of in vitro selected traits have been shown to be expressed in regenerated plants and to be passed on to progeny.

There are several types of in vitro selection that can be used to obtain cells containing the trait of interest (J. Widholm, *Iowa State J. of Research*, 62: 587–597, 1988). These include selection for growth, selection for valuable compound production, auxotroph selection and resistance selection. Selection for resistance should be the easiest kind of selection to accomplish and from the number of reports in the literature this would appear to be true.

The selection for amino acid analog resistance in plants has been pursued for a number of years. A primary focus of this research has been directed to the enzyme anthranilate synthase (AS). AS catalyzes the conversion of chorismate into anthranilate, the first reaction leading from the common aromatic amino acid (shikimate) pathway toward the biosynthesis of tryptophan (Trp). As a branchpoint enzyme in the synthesis of aromatic amino acids, AS plays a key role in the diversion of chorismate into Trp and indolic secondary compound biosynthesis.

Available information indicates that AS plays a key role in regulation of Trp biosynthesis. In plants, bacteria, and fungi, AS activity is regulated by Trp feedback inhibition (Matsui et al., *J. Bacteriol*, 169: 5330–5332, 1987). In microbes, AS usually consists of two nonidentical subunits, referred to as the alpha subunit (component I) and the beta subunit (component II). Component I can convert chorismate to anthranilate in the presence of high levels of ammonia (ammonia-dependent AS activity), whereas component II is responsible for the use of Gln as the amino donor (Hutter et al., *Annu Rev Microbiol*, 40: 55–77, 1986).

As a means to investigate regulation of the Trp pathway, toxic analogs of Trp have been used in metabolic studies of plant cell cultures and as a tool to select mutants. Many of these studies have been conducted with the growth inhibitor 5-methyltryptophan (5MT). In a number of species including *Datura innoxia* (hereinafter referred to as *D. innoxia*), *Catharanthus roseus*, and *Solanum tuberosum*, variant cell lines resistant to inhibitory concentrations of 5MT were found to have AS that was less sensitive to feedback inhibition by Trp (Carlson and Widholm, *Physiol Plant*, 44: 251–255, 1978; Scott et al., *Phytochemistry*, 18: 795–798, 1979; Ranch et al., *Plant Physiol*, 71: 136–140, 1983). Widholm (*Planta*, 134: 103–108, 1977) described 5-methyltryptophan-resistant carrot cell lines and a potato cell line that were auxin autotrophic.

In addition, 5-methylanthranilate was successfully used to isolate plant auxotrophic mutants defective in three different genes, trp1, trp2, and trp3 (Last and Fink, *Science*, 240: 305–310, 1988; Last et al., *Plant Cell*, 3: 345–358, 1991) and mutants of *Chlamydomonas reinhardtii* (Dutcher et al., *Genetics*, 131: 593–607, 1992). Mutants resistant to 5MT or alpha-methyltryptophan (αMT) were reported in *Arabidopsis thaliana* (hereinafter referred to as *A. thaliana*) (Koornneef and van Loenen Martinet, *Arabidopsis Inf Serv*, 20: 104–108, 1983; Kreps & Town, *Plant Physiol*, 99: 269–275, 1992), maize (Kang & Kameya, *Euphytica*, 69: 95–101, 1993), *Lemna gibba* (Tam et al., *Plant Physiol*, 107: 77–85, 1995) and *Oryza sativa* (Lee & Kameya, *Theor Appl Genet*, 82: 405–408, 1991). The specificity of selection with these analogs have not been systematically investigated.

A feedback-insensitive AS gene (ASA1 mutant) has been recently obtained by selection of mutagenized Arabidopsis seeds resistant to 6-methylanthranilate (Li & Last, *Plant Physiol.*, 110: 51–59, 1996). In addition, αMT resistance led to identification of a mutant in *A. thaliana* with the same amino acid change (Kreps et al., *Plant Physiol.*, 110: 1159–1165, 1996).

One method for the production of transgenic plants is to transform plant cells in tissue culture with a plasmid containing a promoter and selectable marker which also contains a gene which would express the desired trait in the regenerated plant. Thus when one selects cells transformed with the selectable marker, many of these cells will also carry the gene that will also be expressed to produce the desired result such as insect resistance, disease resistance, herbicide resistance, changed starch, drought tolerance, etc. An example is where the nptII (neo) gene is driven by a constitutive promoter, nosP (Vermeulen et al., *Plant Cell Reports*, 11: 243–247, 1992). Next to this selectable marker gene is a mutant acetolactate synthase gene with its own promoter. This latter gene makes the regenerated plants resistant to certain herbicides.

The AS gene which encodes for an enzyme that is highly resistant to an amino acid analog, such as 5MT, would be an ideal selectable marker for the production of transgenic plants as described above. Especially if the promoter which regulates the expression of this enzyme provided for high level expression of the enzyme in tissue culture, and little or no expression in regenerated plants. There has been considerable environmental concern because most selectable markers are constitutively expressed in all tissues of the plant and are not of plant origin. The former concern would be reduced by using such a tissue culture specific promoter while the latter concern would be eliminated by using the plant-derived AS gene as the selectable marker. In fact, the use of a tissue culture specific promoter would even allow one to use selectable markers that are not of plant origin.

Traditional selectable markers that are not of plant origin include nptII, which encodes kanamycin resistance.

BRIEF SUMMARY OF THE INVENTION

A first aspect of the present invention is an isolated deoxyribonucleic acid (DNA) molecule comprising a DNA sequence (SEQ ID NO: 4), the ASA2 gene of *Nicotiana tabacum* (hereinafter referred to as *N. tabacum*), and fragments thereof, which encode for a feedback-insensitive form of AS. The ASA2 gene product would function as a selectable marker for transforming plant cells.

A second aspect of the present invention is an isolated DNA molecule comprising a DNA promoter sequence, the ASA2 promoter sequence (SEQ ID NO: 14), which is capable of directing tissue culture specific transcription of a downstream structural gene in a plant cell. The functional promoter sequence may be selected from the group consisting of the tobacco ASA2 promoter and DNA sequences which are at least 70 percent homologous to a fragment of the Tobacco ASA2 promoter which is from about 150 to about 606, more preferably from about 150 to about 370, and most preferably about 150 bases in length. For constitutive expression of the promoter, the fragment is preferably a fragment taken from between about −606 to about −1 of the nucleotide sequence of the ASA2 promoter. For a functional promoter, the fragment preferably includes the −151 to −214 nucleotide sequence of the ASA2 promoter.

The tissue culture specific expression promoter sequence may be selected from the group consisting of the tobacco ASA2 promoter and DNA sequences which are at least 70 percent homologous to a fragment of the Tobacco ASA2 promoter capable of directing tissue culture specific expression. The fragment is preferably between about 30 to about 100, more preferably between about 30 to about 49, and most preferably about 30, bases in length. This fragment is preferably a fragment taken from between about −2252 to about −607 nucleotide sequence of the ASA2 promoter.

A third aspect of the present invention is a DNA construct comprising an expression cassette, which construct comprises, in the 5' to 3' direction, an ASA2 promoter and a structural gene positioned downstream from the promoter and operatively associated therewith.

A fourth aspect of the present invention is an isolated DNA promoter sequence (included in SEQ ID NO: 14) derived by removing a portion of the ASA2 promoter, which is capable of directing high level constitutive transcription of a downstream structural gene in plant tissues. The promoter sequence may be selected from the group consisting of the tobacco ASA2 promoter and DNA sequences which are at least 70 percent homologous to a 606 or smaller fragment of the tobacco ASA2 promoter capable of directing constitutive expression.

A fifth aspect of the present invention is a DNA construct comprising an expression cassette, which construct comprises, in the 5' to 3' direction, the truncated ASA2 promoter (such as the promoter described in the second and fourth aspects of the present invention) and a structural gene positioned downstream from the promoter and operatively associated therewith. Also provided is the method for introducing such a construct into a cell, transforming the cell and expressing the structural gene in the transformed cell. Such a cell may be a plant cell which can be regenerated into a transformed plant which expresses the structural gene.

A sixth aspect of the present invention provides cultured cells and regenerated plants transformed by the constructs of the present invention. The transformed plant may be regenerated from the transformed plant cells.

A seventh aspect of the present invention provides for a method for imparting, to a plant cell, tolerance to an amino acid analog of Trp. The method comprises introducing an expression cassette containing the ASA2 structural gene of the present invention into cells of a wildtype plant to yield transformed plant cells, and expressing the ASA2 in an amount to render the transformed cells substantially tolerant to an amount of an amino acid analog of Trp that inhibits the growth of the untransformed cells of the wildtype plant.

An eighth aspect of the present invention provides for altering the Trp content in a plant by transforming the plant cells with an expression cassette containing the ASA2 structural gene of the present invention, regenerating a differentiated plant from the transformed plant cells wherein the cells of the differentiated plant express ASA2 encoded by the expression cassette in an amount effective to increase the Trp content of the cells of the differentiated plant relative to the Trp content in the cells of the untransformed plant.

A ninth aspect of the present invention provides for a method for producing AS which comprises the steps of: transforming a population of cells with expression cassettes comprising the ASA2 structural gene of the present invention, expressing the ASA2 in the cells.

A tenth aspect of the present invention provides for a method of selecting transformed plant cells which comprises the steps of: introducing into a plant cell an expression cassette comprising the ASA2 structural gene of the present invention which is substantially resistant to inhibition by free L-Trp or an amino acid analog of Trp to yield a transformed plant cell, and culturing the transformed plant cell in an amount of an amino acid analog of Trp, such as 5MT, that inhibits the growth of a corresponding plant cell which does not contain the ASA2 structural gene. This method can also be applied to cells of microorganisms, such as *E. coli*.

The foregoing and other aspects of the present invention are explained in the discussion set forth below.

BRIEF DESCRIPTION OF THE DRAWINGS

FIGS. 4A to 4C show an amino acid sequence alignment of AS genes that was performed by using the Pileup program (Genetics Computer Group, Wisconsin Sequence Analysis Package). Dots within sequences indicate gaps. Asterisks represent a perfect match among these seven different AS sequences. Dots under the sequence indicate a perfect match among six plant AS sequences.

FIG. 9 represents the DNA sequence of the ASA2 promoter fragment (SEQ ID NO: 13)

FIGS. 10A to 10B show GUS expression of tobacco transgenic plants.

FIGS. 15A and 15B show the nucleotide sequence comparison of the N. tabacum ASA2 and ASA3 genomic clones identified in Example 4.

DETAILED DESCRIPTION OF THE INVENTION

Figure 1:
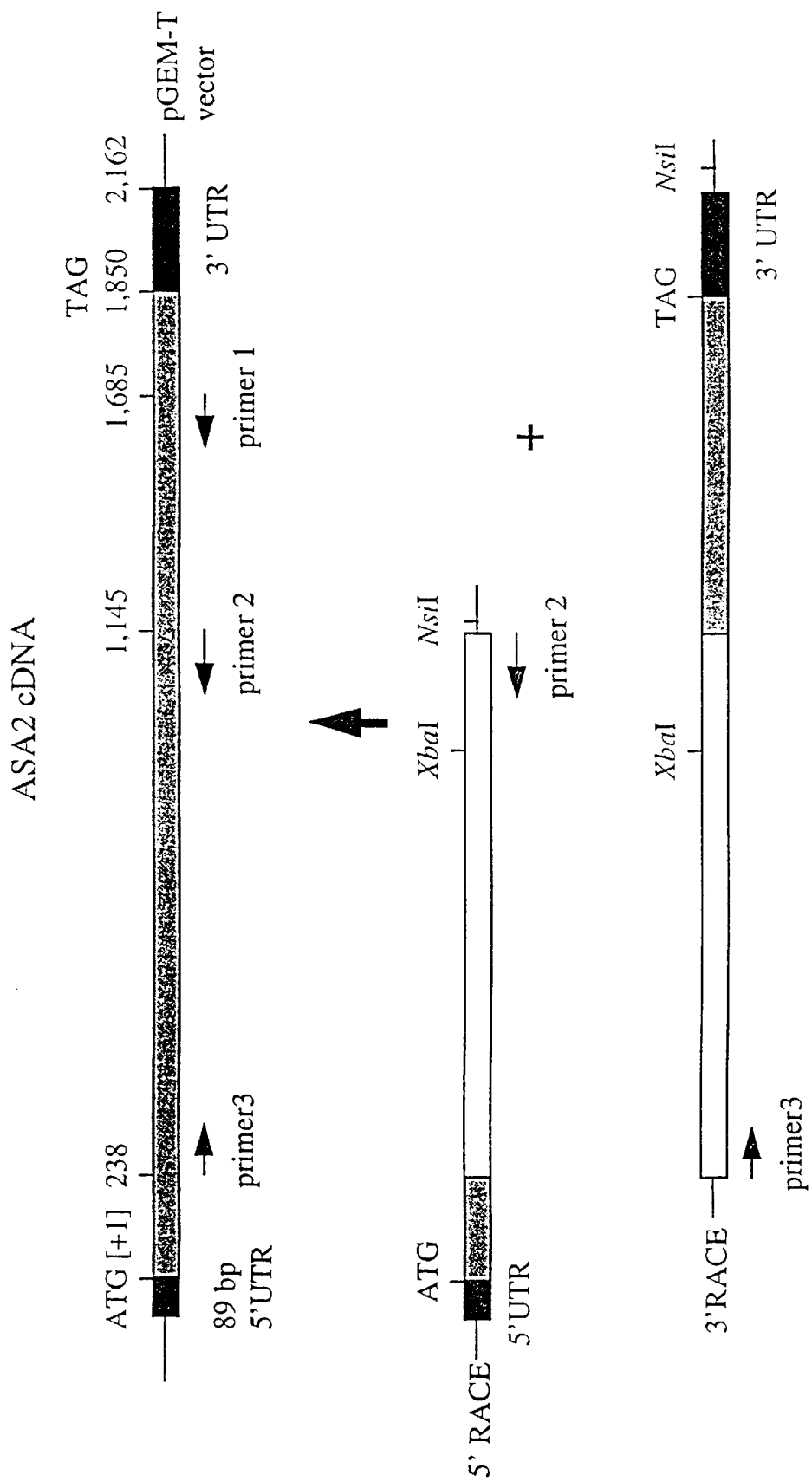
FIG. 1 shows a diagram of the tobacco ASA2 cDNA clone in the pGEM-T vector, the three primers used to isolate 5' and 3' ends of the ASA2 cDNA clones, and the unique restriction enzyme sites required to ligate these two cDNA clones to create the full-length ASA2 cDNA clone. The arrows represent the orientation of each primer. The numbers on the bar represent the nucleotide sequence of the 5' end of each primer. The black bars represent either the 5' or 3' UTR (untranslated region). The white bars represent an overlapping region between the 5' and 3' clones. The region between 5' or 3' UTR and the overlapping region are denoted by gray bars in both fragments.

The present invention provides DNA sequences which encode for the promoter, truncated promoters, and structural gene (ASA2) of the α-subunit of a feedback-insensitive form of the AS enzyme.

According to one aspect of the present invention, the ASA2 structural gene could be contained on a DNA construct under the control of an upstream promoter and downstream terminator sequence, characterized in that the upstream promoter sequence is a DNA sequence that is homologous to the DNA control sequence found upstream of the α-subunit of the feedback-insensitive form of the N. tabacum AS gene, ASA2. The DNA construct may also contain another gene that is not operatively associated with the ASA2 promoter that would provide a desired trait when expressed in the plant. The DNA construct could then be used to select for plant cells in transformation experiments that are 5MT resistant and also contain a gene that would improve on or in some way be desirable in a plant. Other structural genes as described below could be used instead of the ASA2 structural gene.

Another aspect of the present invention relates to promoters of AS genes which are able to drive the transcription of associated DNA sequences preferentially in tissue culture, and not in the tissues of regenerated plants and progeny. Thus, a protein product of the DNA sequences operatively associated with the ASA2 promoter would be produced in greater amounts in tissue culture, with little or no expression in the tissues of a plant. The truncated forms of the ASA2 promoter (such as 606) can also be used to drive high levels of constitutive expression of useful genes in plant tissues. That is, the truncated ASA2 promoters provide constitutive promoters to drive high level transcription of downstream genes in plant tissues. Further, if the tissue culture specific transcriptional sequences are removed, these truncated promoters provide constitutive promoters to drive high level transcription of downstream genes in many plant species.

The selectable marker gene is usually driven by a promoter like the Cauliflower Mosaic virus (CaMV) 35S promoter. Therefore, the gene is expressed in all cells (tissue culture and regenerated plant). This is defined as constitutive expression. There has been considerable environmental concern because most selectable markers are constitutively expressed in all tissues of the plant and are not of plant origin. Because the promoter of the present invention would provide for transcription of associated DNA sequences preferentially in tissue culture, and not in the tissues of the plant, this problem would be removed.

Typically, the selectable marker and the gene that expresses the trait of interest are put on the same plasmid, and in close proximity, so that they are both integrated together into the plant DNA. In addition, the selectable marker and the gene expressing the trait of interest may have their own promoters. If these genes are placed on a plasmid, the order and orientation of these genes is not expected to be important or relevant since plasmids are circular, and each gene is controlled by its own promoter and terminator.

It will be apparent from the discussion in this application and the examples that are described in greater detail below, that other fragments of the ASA2 promoter, longer or shorter than the 2.3 kb fragment originally isolated, or with minor additions, deletions, or substitutions made thereto, can be prepared which will also carry the tobacco ASA2 promoter, all of which are included within the present invention. A further aspect of the present invention includes promoters isolated from other tobacco genes, or from plants other than tobacco as set forth below, which are homologous to the tobacco ASA2 promoter and are capable of directing tissue culture specific transcription of a downstream structural gene in a plant cell.

The ASA2 promoter sequences may be obtained from other plant species by using ASA2 structural gene segments as probes to screen for homologous structural genes in other plants by DNA hybridization under low stringency conditions. Alternatively, regions of the ASA2 structural gene which are conserved among species could be used as PCR primers to amplify a longer segment from a species other than Tobacco, and that longer segment used as a hybridization probe (the latter approach permitting higher stringency screening). An example of high stringency screening is shown in Example 2, below, i.e., the screening involves washing the membranes twice at room temperature with 2× SSC and 0.5% SDS for 20 min. and at 65° C. with 0.1× SSC and 0.1% SDS until background signal disappeared. An example of low stringency screening involves washing the membranes twice at room temperature and at 42° C. for 20 min., respectively, with 2× SSC and 0.5% SDS.

Examples of plant species which may be used in accordance with the foregoing procedures to generate additional ASA2 promoter sequences include *D. innoxia* and potato since hybridization has been noted.

The research which led to the isolation of DNA sequences which encode for tissue culture specific expression of a 5MT resistant form of the AS enzyme began with the generation of 5MT resistant cell lines and the observation that 5MT resistance was lost in regenerated plants. The generation of the initial 5MT resistant cell lines is described in more detail in Example 1.

As described in Example 1, the mechanism of 5MT resistance in *N. tabacum* was different from that observed in other species such as carrot where only one enzyme form was detected in wild-type and 5MT-selected cultured cells (Brotherton et al., *Planta*, 168: 214–221, 1986). Wild-type carrot cells contained a Trp feedback-sensitive AS and 5MT selected carrot cells contained a Trp feedback-insensitive AS, suggesting that a structural mutation was causing insensitivity in the only or principal AS form. Unlike *N. tabacum*, plants regenerated from 5MT-selected *D. innoxia* cultured cells contained Trp feedback-insensitive AS and elevated levels of Trp suggesting a mechanism of 5MT-resistance more like that seen in carrot than in *N. tabacum*.

The decreased feedback control by Trp caused a build up of Trp in cells and plants while the decreased inhibition by 5MT or other Trp analogs (Widholm, *Biochem. Biophys. Acta* 261: 52–58, 1972) led to resistance to these normally toxic compounds. Thus, expression of the ASA2 structural gene in plant cells led to resistance to these analogs (Widholm, *Biochem. Biophys. Acta*, 261: 52–58, 1972), where 5MT-selected cells expressing the ASA2 structural gene grew in media containing 1100 $\mu$M 5MT while unselected cells did not grow in media containing 20 $\mu$M 5MT. This level of resistance to a Trp analog is greater than that reported for other Trp analog-selected cells or plants of other species like carrot (Widholm, *Biochem. Biophys. Acta*, 279: 48–57, 1972), *D. innoxia* (Ranch et al., *Plant Physiol.*, 71: 136–140, 1983), rice (Wakasa & Widholm in *Biotechnology in Agriculture and Forestry*, 14 Rice, Y. P. S. Bajaj (ed.), Springer-Verlag, New York, 304–315, 1991), *Lemna gibba* (Tam et al., *Plant Physiol*. 107: 77085, 1995) and *A. thaliana* (Kreps et al., *Plant Physiol.*, 110: 1159–1165, 1996). AS from 5MT-selected potato cultured cells may be as Trp feedback-insensitive as AS from 5MT-selected tobacco cells, but the gene for this enzyme has not been isolated (Carlson & Widholm, *Physiol. Plant*. 44: 251–255, 1978).

Such as in the case of Li and Last (*Plant Physiol.* 110: 51–59, 1996), they characterized an *A. thaliana* mutant selected using 6-methylanthranilate that contained an altered AS 95% inhibited by 100 $\mu$M Trp. Tobacco cells selected using 5MT and overexpressing the ASA2 structural gene contained AS that is 20% active at 900 $\mu$M (Brotherton et al., *Planta*, 168: 214–221, 1986), as is the AS from the *N. tabacum* cell line of the present invention which is designated AB15-12-1. Because the ASA2 structural gene product, e.g., as produced by the cell line AB15-12-1, of the present invention is much more Trp feedback-insensitive than other identified plant AS, except for an AS found in *Ruta graveolens* (Bohlmann et al., *Plant Physiol*, 111: 507–514, 1996), higher concentrations of Trp analogs could be used for more effective selection. Therefore, the ASA2 structural gene from *N. tabacum* of the present invention which encodes for a feedback-insensitive form of the enzyme would be a much more effective selectable marker in tissue culture transformation experiments than the AS structural gene identified by Li and Last (*Plant Physiol*. 110: 51–59, 1996).

Li and Last (*Plant Physiol*. 110: 51–59, 1996) also identified a single amino acid change (aspartate at position 341 was changed to asparagine) that they suggest results in the Trp feedback insensitivity of the *A. thaliana* mutant AS. In contrast, the tobacco ASA2 structural gene of the present invention produces a protein containing the amino acid sequence phenylalanine$_{107}$-arginine$_{108}$ near a site on AS important to Trp feedback inhibition. The wildtype and mutant Arabidopsis AS proteins and the tobacco ASA1 gene product (FIGS. 4A to 4C) contain serine-glutamine at this point in the aligned sequences, and these amino acids may be the cause of the Trp feedback insensitivity in 5MT-selected tobacco. The changes in the two amino acids (Phe$_{107}$ and Arg$_{108}$) located near a conserved region affecting feedback inhibition are similar to a change found in the amino acid (Arg$_{140}$) in the AS$\alpha$1 of *Ruta graveolens* encoding a feedback-insensitive AS $\alpha$-subunit as described by Bohlmann et al.(*Plant Physiol*. 111: 507–514, 1996).

WO 97/26366, international publication date Jul. 24, 1997, of deKalb Genetics Corporation (herein referred to as "deKalb patent application") discloses maize AS gene and its uses. The application claims that the amino acid sequence at 377, Lys instead of Met, is important for feedback inhibition to Trp.

In contrast, we found that in tobacco ASA2, the amino acids Phe and Arg at positions 107 and 108, respectively, are responsible for feedback insensitivity to Trp and resistance to 5MT. This was confirmed by site-directed mutagenesis of Example 7.

In summary, the main region of the amino acid sequence responsible for feedback insensitivity to Trp and analogs such as 5MT, and degree of feedback sensitivity of AS enzyme against exogenous Trp are different between the maize ASA2 of the dekalb patent application and the tobacco ASA2 of the present application.

Further, the deKalb patent application claims its maize ASA2 sequence is highly homologous to Arabidopsis ASA genes which will allow the maize ASA2 to be used as a probe to hybridize to other AS genes under high stringency conditions.

In contrast, we had failed, despite numerous tries, in using Arabidopsis ASA1 and ASA2 cDNA as probes to hybridize with tobacco genomic DNA. There was no clear hybridization even under low stringency conditions, despite sequence alignment which appeared to show 62% amino acid identity between Arabidopsis and tobacco AS genes. Only under very low stringency conditions, and using 200 bp of the 3' fragment of the Arabidopsis ASA1 cDNA as a probe, did we find very faint hybridization.

If the ASA2 gene (cDNA clone) were driven by the ASA2 promoter of the present invention, then it should only be expressed for selective purposes in cultured cells and not in regenerated plants as demonstrated using the selection and regeneration experimental protocols described in Brotherton et al. (Brotherton et al., *Planta* 168: 214–221, 1986 and Widholm, in *Plant Cell Cultures: Results and Perspectives*, F. Sala, B. Parisi, R. Cella, O. Ciferri (eds.), Elsevier/North Holland Biomedical Press, Amsterdam, pp. 157–159, 1980).

The cloned ASA2 gene may also be overexpressed in *Escherichia coli* (*E. coli*) to obtain large amounts of the enzyme for further study. The protein may be expressed with a 6XHIS tag that facilitates its purification from the E. coli cell extract. The 6XHIS attached to the overexpressed protein through a transcriptional fusion would allow one to purify the protein by binding to Ni-NTA since the His amino acids bind to this complex. There are many other similar strategies including fusing a protein of interest to glutathione-S-transferase and binding this to glutathione-affinity media. The ASA2 protein could then be used to study the Trp binding/inhibition and can be used as an antigen to produce antibodies, both monoclonal and polyclonal, for several uses. Purified antibody to the ASA2 encoded protein could be used in Western Blot analysis of various plant tissues. Somewhere in a normal plant under the appropriate conditions, the ASA2 gene may be expressed at low levels. Western blots and dot blots probed with antibody directed to ASA2 could be used to try to identify or confirm Northern blot results localizing ASA2 expression. Alternatively, antibody could also be used as an immunohistochemical probe to determine when in the plant's life cycle, under what environmental condition, or where in the cell or whole plant is the Trp feedback-insensitive AS expressed.

Antibodies could also be used to study and purify the native protein from wild-type and 5MT-selected cells in order to understand the subunit composition of the enzyme from both types of cells. In addition, antibodies could also be used to study AS from cells and plants of other species including potato, where like in tobacco, 5MT-selection resulted in two separable AS forms.

If the E.coli expressed ASA2 encoded protein is enzymatically active, its feedback characteristics could be studied in several ways. Site-directed mutagenesis would be a direct method to confirm the relationship between a particular amino acid(s) in the protein sequence and Trp feedback insensitivity. Other methods would include mutagenesis followed by selection for Trp analog resistance that should produce random changes in the AS sequence.

The ASA2 cDNA indeed produces a protein when expressed in E. coli that is appreciably more feedback-insensitive to Trp than is Arabidopsis ASA1 enzyme (FIG. 6) indicating that indeed this is a gene for a feedback-insensitive AS and that the amino acid alterations mentioned above are responsible for this.

We have also tested and confirmed that the tobacco ASA2 produces free Trp by using the E. coli system (see Example 7). In Example 7, to study overproduction of free Trp by ASA2, we plated the ASA2 complemented E. coli in the center of 300 μM 5MT-containing minimal medium without Trp and the E. coli cells transformed with site-directed mutagenized ASA2 which was feedback-sensitive, were plated adjacent to the ASA2 complemented E. coli strain. It was found that the E. coli cells transformed with the site-directed mutagenized ASA2 could only grow where they were located close to the E. coli cells transformed with the ASA2 on the 300 μM 5MT-containing minimal medium but without Trp, while the E. coli cells transformed with the site-directed mutagenized ASA2 alone could not grow even on 10 μM 5MT-containing minimal medium without Trp.

The original 5MT-resistant cell lines used as a source to clone the ASA2 gene exhibits 50% enzyme activity of the feedback-insensitive ASA2 at 100 μM Trp. This value is at least six times higher than those found for maize ASA2 (described in the dekalb patent application, above) and mutant Arabidopsis ASA1 enzyme activities. This enzyme activity of tobacco ASA2 was also shown in partially purified tobacco ASA2 using the E. coli system.

To achieve the different aspects of the present invention, methods known in the art may be modified by using the ASA2 gene, ASA2 promoter, and ASA3 gene sequences disclosed in the present application. Such methods are found, e.g., in the deKalb patent application, which is herein incorporated by reference in its entirety. Examples of how such methods may be applied to the present invention are: methods for transforming cells with the genes of the present invention, strategy for selecting the resulting Trp overproducer cell lines, selection and characterization of the resistant cell lines, plant regeneration and production of seeds, and development of Trp overproducer commercial hybrid seeds; formation of an expression cassette containing the sequences disclosed herein, optional and additional DNA sequences to be added into the expression cassette, methods for screening for expression of the AS gene or expression cassette of the present invention; methods of imparting tolerance to an amino acid analog of Trp and/or altering Trp content in the cell or tissue of a plant or microorganism by introducing the genes of the present invention, methods for introducing the genes of the present invention and producing AS; and commercial approaches to Trp extraction from the resulting high Trp seeds, such as maize and soybean seeds. Non-limiting examples of these methods are further described below.

Definitions

As used in the present application, the term "substantial sequence homology" or "homologous" is used to indicate that a nucleotide sequence [in the case of DNA or ribonucleic acid (RNA)] or an amino acid sequence (in the case of a peptide, protein or polypeptide) exhibits substantial functional or structural equivalence with another nucleotide or amino acid sequence. Any functional or structural differences between sequences having substantial sequence homology will not affect the ability of the sequence to function as indicated in the present application. For example, a sequence which has substantial sequence homology with a DNA sequence disclosed to be a plant cell tissue culture specific promoter will be able to direct the plant cell tissue culture specific expression of an associated DNA sequence. Sequences that have substantial sequence homology with the sequences disclosed herein are usually variants of the disclosed sequence, such as mutations, conservative amino acid changes, but may also be synthetic sequences. Structural differences are considered to be negligible if there is a significant sequence overlap or similarity between two or more different sequences or if the different sequences exhibit similar physical characteristics. Such characteristics can include, for example, immunological reactivity, enzyme activity, structural protein integrity, etc.

Two nucleotide sequences may have substantial sequence homology if the sequences have at least 70 percent, more preferably 80 percent and most preferably 90 percent sequence similarity between them. Two amino acid sequences have substantial sequence homology if they have at least 50 percent, preferably 70 percent, and most preferably 90 percent similarity between the active portion of the polypeptides.

In the case of promoter DNA sequences, "substantial sequence homology" also refers to those portions of a promoter DNA sequence that are able to operate to promote the expression of associated DNA sequences. Such operable fragments of a promoter DNA sequence may be derived from the promoter DNA sequence, for example, by cleaving the promoter DNA sequence using restriction enzymes, synthesizing in accordance with the sequence of the promoter DNA sequence, or may be obtained through the use of PCR technology (Nisson et al., *PCR Methods and Applications*, 1: 120, 1991).

Further, as used in this application and claims, the SEQ ID Nos. and disclosed nucleotide sequences include: (1) the DNA sequences as disclosed, (2) the complementary nucleotide sequences (which may be RNA or DNA) to the disclosed sequences or their coding sequences, (3) the corresponding RNA sequences to the listed DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methyl-cytosine replacing cytosine, (6) nucleotide sequences that are homologous to the disclosed sequences, and (7) nucleotide sequences coding for the homologous peptides, polypeptides, or proteins. These sequences may be naturally occurring or synthetic. Since nucleotide codons are redundant, also within the scope of this invention are nucleotide sequences which code for the same proteins or homologous proteins. These latter nucleotide sequences may also be used in the practice of the invention.

Similarly, as used in this application and claims, the SEQ ID Nos. and disclosed amino acid sequences include sequences that are homologous to or have substantial sequence homology to these SEQ ID Nos. and disclosed amino acid sequences. Also within the scope of the present invention are peptides, polypeptides, and proteins which are homologous to those disclosed herein, such as ASA1 and ASA2.

The term "operatively associated" as used herein, refers to DNA sequences on a single DNA molecule which are associated so that the function of one is affected by the other. Thus, a promoter is operatively associated with a structural gene when it is capable of affecting the expression of that structural gene (i.e., the structural gene is under the transcriptional control of the promoter). The promoter is said to be "upstream" from the structural gene, which is in turn said to be "downstream" from the promoter.

Conversely, "not operatively associated" as used herein, refers to DNA sequences on a single DNA molecule which are not associated so that the function of one is not affected by the other. Thus, the ASA2 promoters of the present invention can be used with or without being operatively associated with the "useful gene" on the DNA construct described below.

DNA constructs of the present invention may include 5' to 3' in the direction of transcription, a promoter of the present invention and a structural gene operatively associated with the promoter. The structural gene may be the 5MT resistant form of the AS from N. tabacum of the present invention or any of the other selectable markers described below. Another DNA construct that may be constructed would also include a gene that when expressed affects the plant in a desired way. As described below, this gene may or may not be operatively associated with the promoter of the present invention.

Structural genes are those portions of genes which comprise a DNA segment coding for a peptide, protein, polypeptide, or portion thereof, possibly including a ribosome binding site and/or a translational start codon, but lacking a promoter. The term can also refer to copies of a structural gene naturally found within a cell but artificially introduced. The structural gene may encode a protein not normally found in the plant cell in which the gene is introduced or in combination with the promoter in which it is operationally associated, in which case it is termed a heterologous structural gene.

The structural gene that would be operatively associated with the promoter of the present invention is most preferably the ASA2 gene encoding the a-subunit of the 5MT resistant form of AS from tobacco (N. tabacum). The structural gene could function as a selectable marker in plant cell tissue culture transformation, allowing one to identify plant cells harboring the DNA construct containing the selectable marker and the gene that affects the plant in some desired way. Unlike other selectable markers described below, this selectable marker of the present invention is of plant origin. Commonly used selectable markers provide protection against antibiotics, toxins, heavy metals, and the like. Genes which may be employed as selectable markers include neomycin phosphotransferase (nptII) which provides kanamycin resistance; hygromycin phosphotransferase (hpt) which provides hygromycin resistance; and phosphinothricin-acetyl transferase which provides phosphinothricin resistance. Expression of antibiotic detoxifying genes in plants is a concern since it could lead to antibiotic resistant forms of plants and this antibiotic resistance could be spread to microorganisms. Likewise, herbicide resistance could be spread to weeds. In addition, possible allergic reactions to foreign proteins expressed in plants could be alleviated if the selectable marker were of plant origin or not expressed in the plant as would be the case if the selectable marker were under the control of the promoters of the present invention.

The structural gene of the present invention that may or may not be operatively associated with the promoter of the present invention on a DNA construct is described next. Genes of interest for use in plants include those affecting a wide variety of phenotypic and non-phenotypic properties. Some phenotypic properties commonly selected for include resistance to herbicides, disease, salt, metals, high or low pH, flooding, heat, cold, drought, insects and low nutrients. These genes may be obtained from prokaryotes, eukaryotes or archaebacteria and may be synthesized in whole or in part. Other structural genes are further described below, using the truncated ASA2 promoters as examples, though these structural genes could also be used with the full promoter.

The recombinant DNA vectors of the present invention are those vectors that contain sequences of DNA that are required for the transcription of cloned copies of genes and for the translation of their mRNA's in a host. The recombinant DNA vectors typically have at least one origin of replication. For convenience, it is common to have a replication system functional in E. coli such as ColE1, pSC101, pACY184, or the like. In the present invention, such vectors as pGEM5, pBluescript SK- and pUC19 were used.

Plant cells may be transformed with the DNA constructs of the present invention according to a variety of known methods including particle bombardment of cells or tissues with a device such as the particle inflow gun (Vain et al., *Plant Cell Tissue Organ Culture*, 33: 237–246, 1993), electroporation of protoplasts (Shillito et al., *Bio/Tech* 3: 1099–1103, 1985), and agrobacterium mediated transformation (Vermeulen et al., *Plant Cell Reports*, 11: 243–247, 1992) if the promoter and selectable marker and/or gene of interest are placed into the correct plasmid in the bacterium. The transformed cells may then in suitable cases be regenerated into whole plants in which the new nuclear material is stably incorporated into the genome. Both transformed monocot and dicot plants may be obtained in this way, although the latter are usually more easy to regenerate.

Any plant tissue capable of subsequent clonal propagation, whether by organogenesis or embryogenesis, may be transformed with a vector of the present invention. The term "organogenesis" as used herein, means a process by which shoots and roots (organs) are developed sequentially from meristematic centers; the term "embryogenesis", as used herein, means a process by which shoots and roots develop together in a structure similar to an embryo in a concerted fashion (not sequentially), whether from zygotic or somatic cells or gametes. The particular tissue chosen will vary depending on the clonal propagation systems available for, and best suited to, the particular species being transformed. Exemplary tissue targets include leaf disks, pollen, embryos, cotyledons, bypocotyls, megagametophytes, callus tissue, existing meristematic tissue (e.g., apical meristems, axillary buds, and root meristems), and induced meristem tissue (e.g., cotyledon meristem and hypocotyl meristem).

The ASA2 structural gene of the present invention could be used to transform either monocot or dicot plant species in order to increase intracellular free Trp, which is of nutritional value. In addition, these transformed plants and cells would be candidates for investigating the effect of the ASA2 gene product on AS characteristics and metabolism.

The ASA1 cDNA clone also disclosed herein can be used for comparison with the ASA2 cDNA clone since ASA1 encodes a feedback-sensitive AS. This is shown by the nucleotide sequence that reveals ASA1 to be similar to *A. thaliana* ASA1 and different from the tobacco ASA2.

The promoter sequences disclosed herein may be used to express a structural gene, such as the ASA2 gene encoding the α-subunit of the feedback-insensitive form of AS, in any plant species capable of utilizing the promoter. Other structural genes are described above. Additional structural genes are further described below, using the truncated ASA2 promoters as examples, though these structural genes could also be used with the full promoter. These would include both monocot and dicot plant species. The ASA2 promoter of the present invention should be capable of functioning in any system where relatively undifferentiated cells in culture are used for the selection.

The ASA2 promoter and its truncated versions can be used in place of CaMV 35S for driving the genes generally driven by CaMV 35S. The constructs containing the promoters of the present invention and any downstream genes may be constructed using techniques described herein or modifications thereof which will be obvious to one skilled in the art based on the teaching of this application.

In addition, the truncated versions of the tobacco ASA2 promoter and promoter homologous to it which can drive high level transcription in many tissues of plants of some species (constitutive expression) are useful as promoters for many downstream structural genes. Examples of such truncated versions of the tobacco ASA2 promoter are the 606 fragment and promoters homologous to it. In the transient expression assays of FIG. 8 (and Example 3, below), the 606 fragment showed the highest expression in leaves while reducing the ASA2 promoter to 370 bp gave the resulting fragment a somewhat lower level of expression. In experiments using the protocols of Example 3, it was found that smaller fragments of the tobacco ASA2 promoter, i.e., a 151 fragment (from position −1 to −151) and a 214 fragment (from position −1 to −214) also provide constitutive expression (data not shown). The 214 fragment has double the expression level of the 151 fragment Thus, using the teaching in this application, one skilled in the art can determine, without undue experimentation, a fragment of the promoter that will produce a desired constitutive expression. At the very least, a fragment from about −151 to about −606 of the ASA2 promoter, and fragments homologous to it are expected to control constitutive expression. These fragments, in addition to the full ASA2 promoter, may be used in a construct to transform and produce cultured cells and regenerated plants using methods known in the art. For example, these fragments may be used, in place of the full ASA2 promoter, in the construct in Example 6 to produce cultured cells and regenerated plants which express a downstream structural gene with desired characteristic(s).

Non-limiting examples of the downstream structural genes are genes of various kinds which could be used for plant improvement or modification, some of these are structural genes described above. Other non-limiting examples of the downstream structural genes include: genes that might make plants resistant to diseases [e.g., the *Phaseolus vulgaris* Ch 18 (chitinase) gene (Broglie et al., *Sci.* 254: 1194–1197, 1991)]; resistant to insects [e.g., the *Bacillus thuringiensis* (hereinafter referred to as *B. thuringiensis*) cry1AC gene (Stewart et al., *Plant Physiol.* 112: 121–129, 1996)]; resistant to drought [e.g., the *Vigna aconitifolia* P5CS (Pyrroline-5-carboxylate synthetase) gene (Kishor et al., *Plant Physiol.* 108: 1387–1394 (1995)]; or resistant to herbicide [e.g., the csr1-1 gene from *A. thaliana* (acetolactate synthase) (Vermeulen et al., *Plant Cell Reports* 11: 243–247, 1992)] among many other possibilities. For example, the expression noted for 606 in Example 3, below, was as good as or better than the CaMV 35S promoter that has been used to drive high level transcription of many genes, for example an insect resistance gene, cry1Ac from *B. thuringiensis*, in soybean and cause the soybean plants to be resistant to four different insects (Stewart et al., *Plant Physiol.* 112: 121–129, 1996). As a non-limiting example of an expression construct, the truncated 0.6 kb ASA2 promoter fragments (SEQ ID NO: 14) can be attached to many possible useful genes to be expressed in plants since this portion of the ASA2 promoter drives constitutive expression of genes in many species (Table 2, FIG. 8). The transformation would be accomplished as explained in Example 5, below. The 606 promoter drives high levels of constitutive expression of structural genes placed downstream in plant tissues so various genes can be then expressed to impart many useful traits such as insect resistance if a gene such as the *B. thuringiensis* cry1AC is expressed (Stewart et al., 1996) and other traits as described above.

The 606 promoter and promoters homologous to it will drive expression in cultured cells so they can also be used to drive selectable marker genes. The expression in tissue cultures would also allow one to express genes in cultured cells to show that these genes can be expressed and to determine the effect on the cells. The gene product could also be isolated for other studies. Since these promoters are of plant origin, there should not be a real or perceived environmental problem if the promoters are present in plants.

The invention may be better understood with reference to the accompanying examples, which are intended for purposes of illustration only and should not be construed as in any sense limiting the scope of the invention as defined in the claims appended hereto.

EXAMPLE 1

Plant Regeneration from 5MT Resistant Cell Lines
A. Selection and Plant Regeneration As described in further detail in Widholm (in *Plant Cell Cultures: Results and Perspectives*, F. Sala, B. Parisi, R. Cella, O. Ciferri (eds.), Elsevier/North Holland Biomedical Press, Amsterdam, pp. 157–159, 1980) and Brotherton et al.

(*Planta* 168: 214–221, 1986), suspension cultured *N. tabacum* cells were selected for 5MT resistance by growing about 3×10⁶ cells (one gram fresh weight) in each flask in the presence of a completely inhibitory concentration of the Trp analog (46 μM). Some cells grew in some flasks in 60 days and these continued to grow if placed in 229 μM 5MT. Plants were regenerated by placing some cells onto an agar-solidified medium containing the plant growth regulators, 1.0 mg/l indole-3-acetic acid (Sigma Chemical Company, St. Louis, Mo.) and 0.64 mg/l kinetin (Sigma Chemical Company), instead of 0.4 mg/l 2, 4-dichlorophenoxyacetic acid (Sigma Chemical Company) that was in the suspension culture medium. Shoots that formed in about a month were rooted in solid medium with no growth regulators.

B. Demonstration that 5MT Resistance is Lost in Regenerated Plants

As further described in Widholm (in *Plant Cell Cultures: Results and Perspectives*, F. Sala, B. Parisi, R. Cella, O. Ciferri (eds.), Elsevier/North Holland Biomedical Press, Amsterdam, pp. 157–159, 1980), *N. tabacum* L. cv. Xanthi suspension cultures were selected for 5MT resistance. The selected cells grew in the presence of 229 μM 5MT, contained a Trp feedback-insensitive AS and elevated levels of intracellular free Trp. Leaves of six plants regenerated from this 5MT-selected cell line did not contain a detectable level of the Trp feedback-insensitive AS, but cultures reinitiated from leaf pieces from these plants were again 5MT-resistant, contained the Trp feedback-insensitive AS and had elevated levels of Trp. Brotherton et al. (*Planta* 168: 214–221, 1986) reported that extracts of shoot tips, stems and roots of another set of plants regenerated from 5MT resistant tobacco cultures did not contain kinetically detectable levels of Trp feedback-insensitive AS. Using Sephacryl S-200 chromatography or steric exclusion high performance liquid chromatography, two forms of AS were separated from extracts of 5MT-selected and wild-type cultured cells. The 5MT-selected cultured cells contained more of the Trp feedback-insensitive AS than did the wild-type cells. No Trp feedback-insensitive AS could be detected in extracts of plants regenerated from either 5MT-selected or wild-type cell lines using Sephacryl S-200 chromatography. These results were interpreted to support the hypothesis that the two forms of AS present in wild-type and 5MT-selected cultured cells were two unique enzymes whose expression was independently regulated. This mechanism of 5MT resistance was different from that observed in other species such as carrot where only one enzyme form was detected in wild-type and 5MT-selected cultured cells (Brotherton et al., *Planta* 168: 214–221, 1986). Wild-type carrot cells contained a Trp feedback-sensitive AS and 5MT-selected cells contained a Trp feedback-insensitive AS suggesting a structural mutation causing insensitivity in the only or principal AS form. Unlike *N. tabacum*, plants regenerated from 5MT-selected *D. innoxia* cultured cells contained Trp feedback-insensitive AS and elevated levels of Trp suggesting a mechanism of 5MT-resistance more like that seen in carrot than in *N. tabacum*.

EXAMPLE 2

Cloning and Characterization of the ASA2 gene

A. Preparation of Plant Total RNA for Cloning

The 5MT-resistant tobacco (*N. tabacum*) suspension cell line, AB15-12-1 was used as the source of plant material. The AB lines originated from progeny of one plant regenerated from unselected *N. tabacum* cv. Xanthi tissue cultures. Callus induced from the leaf of the AB-15-12-1 plant, tested resistant to 5MT, and has been maintained until now with both MX medium (Murashige & Skoog, *Physiol. Plant.* 15: 431, 1962, containing 0.4 mg/l 2,4-dichlorophenoxyacetic acid) containing 300 μM 5MT and 5MT-free MX medium. The AB-15-12-1 cell line maintained in MX medium containing 300 μM 5MT (A.T.C.C. Accession Number 209176) was used for the preparation of plant total RNA for cloning below.

Plant total RNA was prepared from one-week-old AB15-12-1 suspension cultured cells by using a combination of a phenol extraction method (McCarty, D. R., et al., *Maize Genetics Coop, Newslett.* 60, 61, 1986 and Ausubel et al., *Current Protocol in Molecular Biology*, New York: Greene Publishing Associates and Wiley-Interscience, 1989) and CsCl-gradient purificaton (Sambrook et al., Molecular Cloning, 2nd ed., Cold Spring Harbor Laboratory Press, 1989).

Tobacco AS cDNAs were isolated by using 5' and 3' RACE (Rapid Amplification of cDNA End System, Gibco BRL, Grand Island, N.Y.) and cloned into the pGEM-T vector (Promega, catalog #A360, Madison, Wis.).

B. Cloning the ASA2 Gene (SEQ ID NO: 4)

FIG. 1 shows a diagram of the tobacco ASA2 cDNA clone in the pGEM-T vector, the three primers used to isolate 5' and 3' ends of the ASA2 cDNA clones, and the unique restriction enzyme sites required to ligate these two cDNA clones to create the full-length ASA2 cDNA clone. Because we isolated a 5' end truncated tobacco ASA1 cDNA before isolating the ASA2 cDNA, primers for cloning the 5' end of the ASA2 cDNA were designed based on the sequence of the tobacco ASA1 cDNA clone (SEQ ID NO: 24).

For 5' RACE, first stranded cDNA was synthesized with primer 1 (SEQ ID NO: 1). A nested PCR was performed with primer 2 (SEQ ID NO: 2). The first stranded cDNA was used as a template for the nested PCR. The PCR reaction was prepared with a final concentration of 0.2 mM of primer (primers 1 and 2 as explained above), 2.5 mM $MgCl_2$, 0.2 mM dNTP mixture and 2.5 units of Taq DNA polymerase. Two sets of thermocycling conditions were programmed by using a PTC-100 (Programmable Thermal Controller, MJ Research, Inc, Watertown, Mass.). Additional denaturation at 94° C. for 5 min and at 80° C. for 3 min. was performed before starting the thermocycling. Taq DNA polymerase was added at 80° C. The first 10 cycles were programmed for denaturation at 94° C. for 1 min., annealing at 50° C. for 2 min., and extension at 72° C. for 2 min. The second 20 cycles were programmed for denaturation at 94° C. for 1 min., annealing at 45° C.+0.4° C. (0.4° C. increasing at each cycle) for 2 min., and extension at 72° C. for 2 min. Additional extension at 72° C. for 10 min. was performed after 30 cycles.

An approximately 1.1 kb fragment was detected by Southern hybridization with tobacco ASA1 and Arabidopsis ASA1 (pKN41/XhoI, 1.8 kb) and ASA2 cDNA clones (pKN108A/BamHI, 2.0 kb) (Niyogi & Fink, *The Plant Cell*, 4: 721–733, 1992) as probes by using a Megaprime DNA labelling system (Amersham) with [α-³²P]dCTP (3000 Ci/mmol). Southern hybridization was done at 42° C. with a hybridization solution (50% formamide, 5× SSPE, 5× Denhardt's solution, 0.1% SDS, and 100 μg/ml salmon sperm DNA). The membranes were washed at high stringency. This involved washing the membranes twice at room temperature with 2× SSC and 0.5% SDS for 20 min. and at 65° C. with 0.1× SSC and 0.1% SDS until background signal disappeared. This tobacco ASA2 5' end cDNA fragment was cloned into commercially available pGEM-T vector (Promega) and sequenced by the Genetic Engineering Lab, University of Illinois at Urbana-Champaign.

Most of the procedures to isolate the 3' end of the tobacco ASA2 cDNA were the same as for 5' RACE except for primers and dATP tailing at the 5' end of the cDNA. Primer 3 (SEQ ID NO: 3) was designed based on the sequence of the 5' ASA2 cDNA clone. An approximately 1.9 kb fragment was detected by Southern hybridization with the 5' ASA2 cDNA clone as a probe, cloned into the pGEM-T vector, and sequenced (FIGS. 4A to 4C).

The sequencing results analyzed by the BLAST program showed that these two clones are the same AS gene, since the nucleotide sequences of an 828 bp overlapping region (indicated as a white bar in FIG. 1) perfectly matched. There is only one XbaI site in the 828 bp overlapping region, only one NsiI site in pGEM-T vector, and no NsiI site in both 5' and 3' fragments. The 5' cDNA clone in pGEM-T vector was digested with XbaI and NsiI to remove the 3' end of the sequence downstream of the XbaI site, which is approximately 318 bp including 57 bp of multiple cloning site. The 3' cDNA clone was digested with XbaI and NsiI to isolate the 3' end fragment of the ASA2 gene (approximately 1.4 kb including 16 bp poly(A) and 57 bp of the multiple cloning site), which was cloned into the 5' end of the ASA2 gene in pGEM-T vector. These two fragments were ligated to create the full-length tobacco ASA2 cDNA (A.T.C.C. Accession Number 209152).

Figure 2:
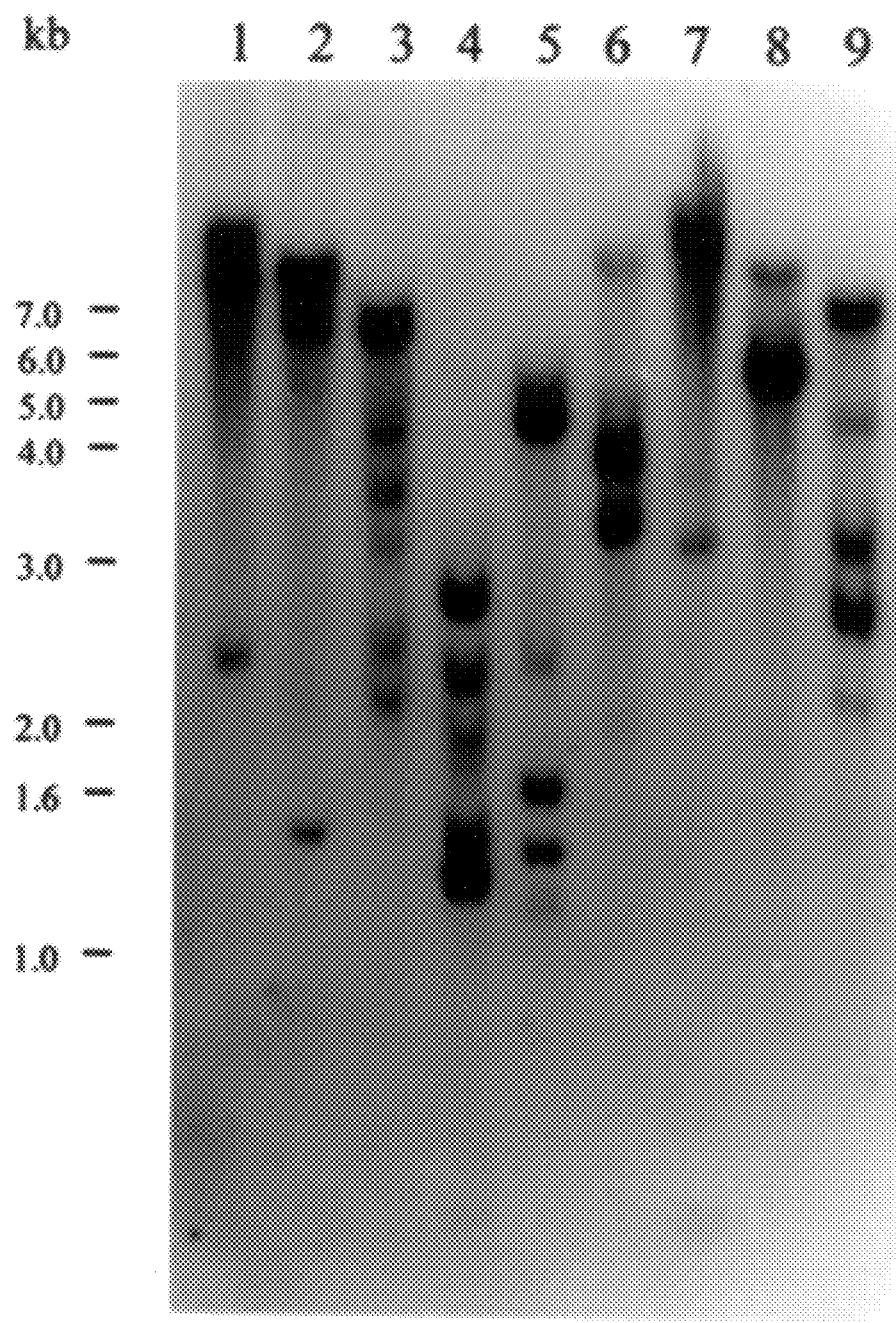
FIG. 2 shows a Southern hybridization of AB15-12-1 genomic DNA. The DNA was digested with nine different restriction enzymes (lane 1 to 9: BamHI, EcoRI, EcoRV, HincII, HindIII, KpnI, PstI, ScaI, and XbaI in order) and probed with the full-length (2.16 kb) ASA2 cDNA fragment.

The full-length (2.16 kb) ASA2 cDNA fragment including 5' and 3' UTR was used as a probe to determine how many ASA2 genes exist in the tobacco genome by using Southern hybridization (FIG. 2). Twenty μg of AB15-12-1 genomic DNA isolated by using CsCl-gradient purification (Ausubel et al., *Current Protocol in Molecular Biology*, New York: Greene Publishing Associates and Wiley-Interscience, 1989 and Sambrook et al., *Molecular Cloning*, 2nd ed., Cold Spring Harbor Laboratory Press, 1989) were digested with nine different restriction enzymes (lane 1 to 9: BamHI, EcoRI, EcoRV, HincII, HindIII, KpnI, PstI, ScaI, and XbaI in order), followed by electrophoresis in a 0.8% agarose gel at 30 volts overnight. Southern hybridization was performed at 42° C. Membranes were washed at high stringency as described before.

C. mRNA Expression of the ASA2 Gene

Figure 3:
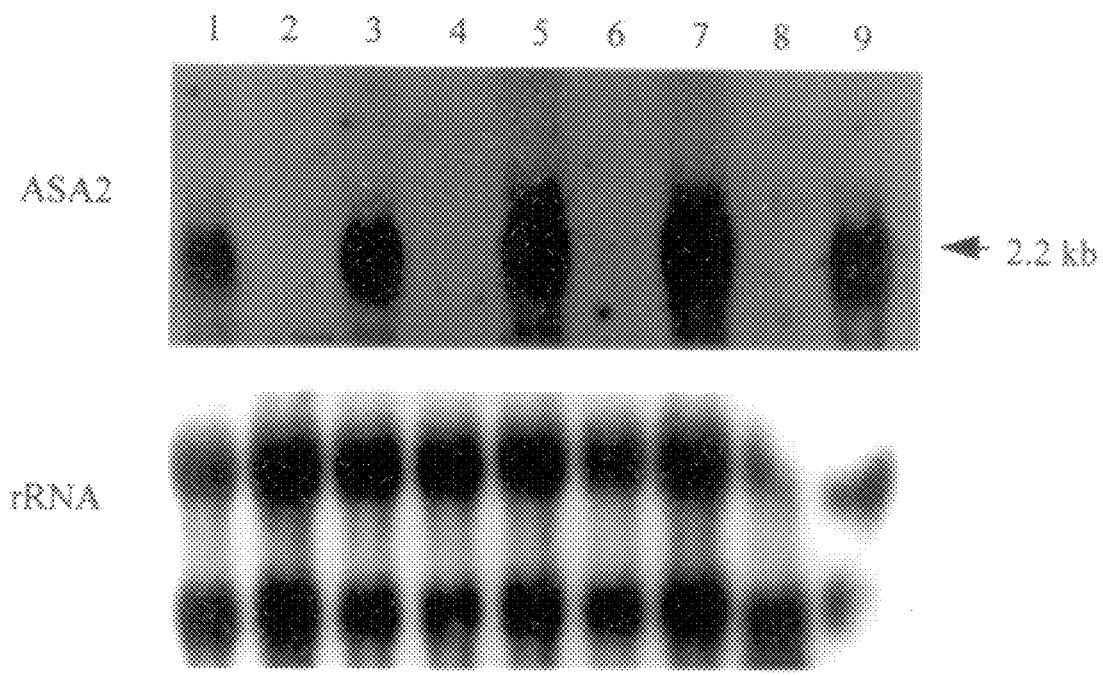
FIG. 3 illustrates mRNA expression of the tobacco AS genes. mRNA expression was detected with the tobacco ASA2 cDNA clone (full-length cDNA) and a ribosomal RNA as probes.

FIG. 3 illustrates mRNA expression of the tobacco AS genes. mRNA expression was detected with the ASA2 cDNA clone (full-length cDNA described above) and ribosomal RNA as probes. Lane 1, 3, 5, and 7 represent four different 5MT-resistant *N. tabacum* cell lines. Lane 1 and 7 are 5MT-resistant AB15-12-1 cell lines which have been maintained for at least four years in MX medium without 5MT and with 300 μM 5MT, respectively. Lanes 3 and 5 were recently selected 5MT-resistant tobacco cell lines maintained in 300 μM 5MT-containing medium. Lane 9 represents a 5MT-resistant *Nicotiana sylvestris* cell line which had been maintained in 300 μM 5MT containing medium for at least one year. Lane 2, 4, and 6 represent three different 5MT-sensitive *N. tabacum* cell lines. Lane 8 represents mRNA extracted from leaves of a plant regenerated from the AB15-12-1 cell line. For these studies, total RNA was isolated from one-week-old suspension cultured cells and leaves harvested from three-week-old seedlings. Ten to 20 μg of total RNA were extracted by using a phenol extraction method, electrophoresed in a denaturing formaldehyde gel, and blotted onto N+-hybond membrane following a general capillary transfer method (McCarty, E. R., 1986, supra, Ausubel et al., 1989, supra, and Sambrook et al., 1989, supra). Northern hybridization and washing of membranes were performed under the same conditions as for Southern hybridization described above (Example 2, Section B).

D. Southern Hybridization

The full-length ASA2 cDNA clone hybridized to multiple bands in AB15-12-1 genomic DNA digested with nine different restriction enzymes (FIG. 2). This result indicated that there was more than one ASA2 like genes in tobacco. This result was understandable, since *N. tabacum* was an allotetraploid.

The tobacco ASA2 cDNA clone hybridized very weakly to Datura and potato under high stringency conditions (data not shown). These results suggest that it may be possible to select 5MT-resistant cell lines from these plants which may carry similar characteristics to AB15-12-1. It may also be possible to isolate feedback-insensitive AS genes from these plants by using tobacco ASA2 cDNA as probe.

The tobacco full-length ASA2 clone detected an approximately 2.2 kb transcript only in 5MT-resistant suspension cultured cells (FIG. 3). 5MT-sensitive suspension cultured cells and leaves did not show expression of the ASA2 gene at the mRNA level under the condition of overnight exposure of X-ray film with an intensifying screen.

These results indicated that the ASA2 gene may encode a feedback-insensitive AS that was tissue-specific and detected very strongly in only 5MT-resistant tissue cultured cell lines.

E. Amino Acid and Nucleotide Sequence Analysis of the ASA2 Gene

SEQ ID NO: 4 is the ASA2 nucleotide sequence including 5' UTR (nucleotides 1 to 89) and 3' UTR (nucleotides 1941 to 2144). The translation start codon (ATG) begins at nucleotide position 90. The translation stop codon (TAG) ends at nucleotide position 1940. The coding region in SEQ ID NO: 4 corresponds to nucleotides 90 to 1,940. The ASA2 amino sequence is presented in SEQ ID NO: 5 and corresponds to translation of nucleotides 90 to 1940 of SEQ ID NO: 4.

The ASA2 amino acid sequence (SEQ ID NO: 5 and also shown as aligned to SEQ ID NO: 25) was compared to other AS genes from plants and prokaryotes, and the five best matches were chosen based on BLAST analysis (Altshul et al., *J. Mol. Biol.*, 215: 403–410, 1990). An amino acid sequence alignment with these AS genes was performed by using Pileup program (Genetics Computer Group, Wisconsin Sequence Analysis Package) and is shown in FIGS. 4A to 4C. TASA1 SEQ ID NO: 23, (predicted amino acid sequence from the nucleotide sequence of SEQ ID NO: 24), TASA2 (SEQ ID NO: 5), RASA1, RASA2, AASA1, AASA2, and CTRPE correspond to *N. tabacum* ASA1 and ASA2, *Ruta graveolens* ASα1 and ASα2 (Bohlmann, J. et al., *Plant J.* 7(3): 491–501, 1995), *A. thaliana* ASA1 and ASA2 (Niyogi & Fink, 1992), and *Clostridium thermocellum* trpE (Sato, S. et al., *J. Biochem.* 105: 362–366, 1989) cDNA clones, respectively. Dots within sequences indicate gaps. Asterisks represent a perfect match among these seven different AS sequences. Dots under the sequence indicate a perfect match among six plant AS sequences. There was no sequence for *N. tabacum* ASA1 from nucleotides 1 to 125 when aligned in FIGS. 4A to 4C, since a truncated 5' end of the ASA1 cDNA clone was obtained. Even though *N. tabacum* ASA1 cDNA clones (5' and 3' end cDNAs) were not ligated because of a difference of two nucleotides in an overlapping region between 5' and 3' clones, the ASA1 amino acid sequence was used to align in order to compare sequence similarity to other AS genes. These two nucleotides created amino acid $Pro_{243}$ in the 5' clone and $Asn_{243}$ in the 3' clone which is indicated by a plus (+) on the top of the amino acid in FIGS. 4A to 4C. *N. tabacum* ASA2 has a transit peptide sequence (approximately 60 amino acids)

downstream of the translation initiation codon which does not have any homology to the transit peptide sequences of other AS genes. Conserved amino acids for feedback sensitivity in AS of other species have not been changed in the N. tabacum ASA2 gene, which are indicated by bold letters and asterisks on the top of the amino acids. A single amino acid change in an Arabidopsis AS mutant ($Asp_{341}$ to $Asn_{341}$: indicated by bold letter and underlining in FIGS. 4A to 4C—at position 363 when aligned in the figures) which causes feedback insensitivity (Li & Last, *Plant Physiol.* 110: 51–59, 1996) was not found in the N. tabacum ASA2 gene in FIGS. 4A to 4C (SEQ ID NO: 4). However, we have identified two amino acids ($Phe_{107}$ and $Arg_{108}$ : indicated by bold letter and underlining in FIGS. 4A to 4C at positions 142 and 143 when aligned in the figure) of the N. tabacum ASA2 amino acid sequence in FIGS. 4A to 4C (SEQ ID NO: 5), which possibly affect the Trp binding site in N. tabacum ASA2, resulting in feedback insensitivity.

The predicted amino acid sequence of the N. tabacum ASA2 gene showed 72%, 68% and 67%, 68% and 61% and 32% and amino acid identity to the N. tabacum ASA1, A. thaliana ASA1 and ASA2 (Niyogi & Fink, 1992) and R. graveolens ASα1 and ASα2 (Bohlmann, J. et al., 1995), and C. thermocellum trpE gene (Sato, S. et al., 1989), respectively, while the N. tabacum ASA1 cDNA clone exhibits 98% amino acid identity to the Arabidopsis ASA1 (Table 1).

3. E. coli expression of ASA2 Gene

The tobacco ASA2 gene was expressed in E. coli strain trpE5972, a mutant line containing a nonsense trpE gene, grown to late log phase on Luria Bertani medium with 100 μM Trp. Expression was induced by addition of 100 μM isopropylthiogalactoside and a protease inhibitor, 135 μM phenylmethylsulfonylfluoride (PMSF) was added with further incubation for three hours at 30° C., 150 rpm. The cells were collected by centrifugation and resuspended in 50 mM Tris, 5 mM $MgCl_2$, 100 mM $NH_4Cl$, 2 mM dithiothreitol, 20% glycerol, pH 8.0 plus 100 μM PMSF and disrupted using a French press (2 passes, 20,000 psi). Cell debris was removed by centrifugation and the supernatant treated with Ni-affinity resin. Bound protein was eluted with 100 μM imidazole in pH 6.3 buffer. The Arabidopsis ASA1 gene was similarly expressed except that the E. coli strain JM109 was used and enzyme activity in a crude cell extract without Ni-affinity purification was characterized.

Enzyme activity with and without Trp in 50 mM Tris, 5 mM $MgCl_2$, 1 mM EDTA, 100 mM $NH_4Cl$, 2 mM dithiothreitol, 20% glycerol, pH 7.8 plus 100 μM chorismate. Anthranilate produced in 30 min at 30° C. was extracted using ethyl acetate and fluorescence measured at excitation 340 and emission 400.

Figure 6:
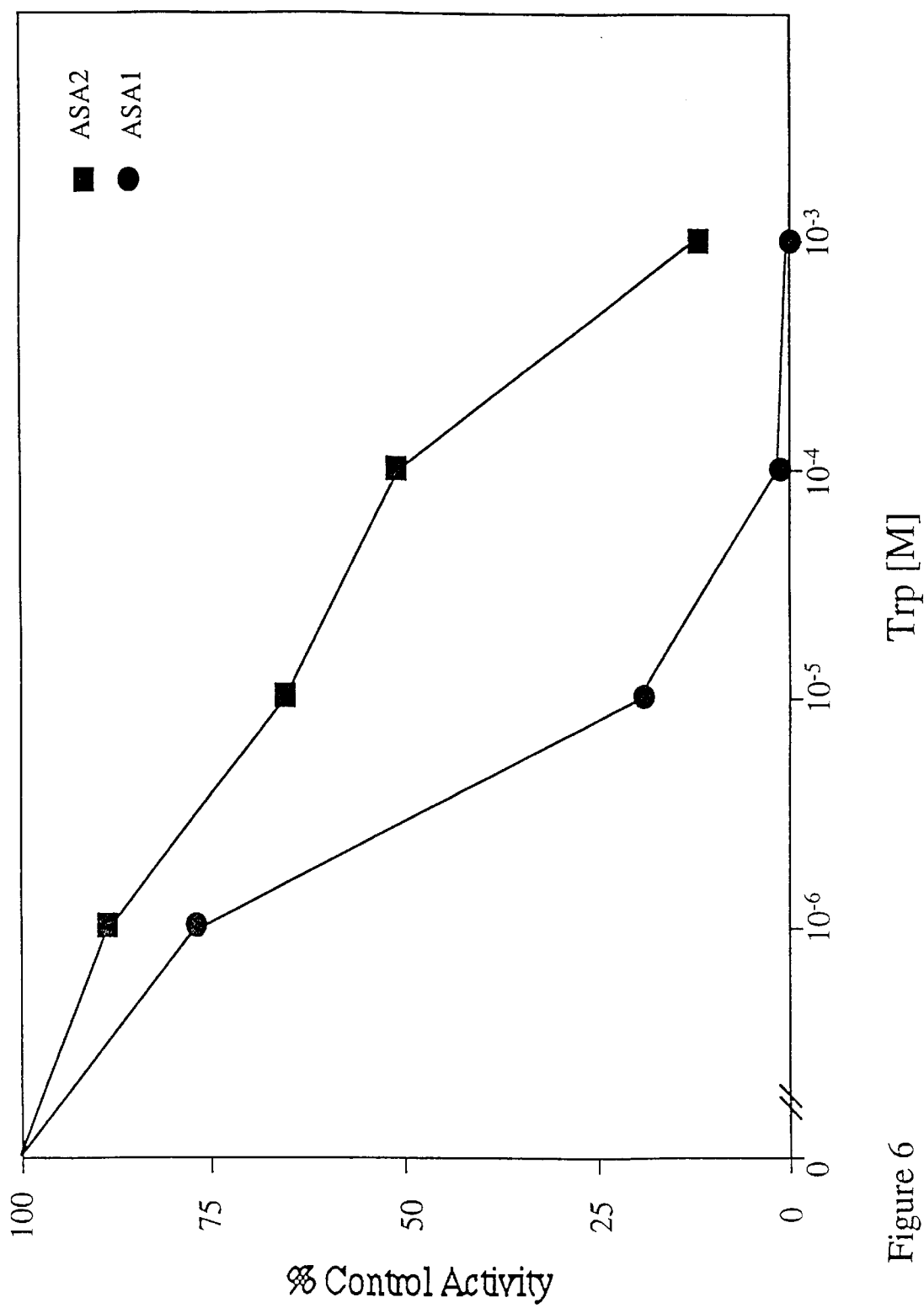
FIG. 6 shows feedback inhibition assay of tobacco ASA2 and Arabidopsis ASA1 activities expressed in E. coli.

FIG. 6 shows that the partially purified ASA2 gene expressed in E. coli is still active at 100 μM Trp (50%). The Arabidopsis ASA1 gene product is completely inhibited at

TABLE 1

|       | *TASA1  | TASA2 | RASA1 | RASA2 | AASA1 | AASA2 | CTRPE |
|-------|---------|-------|-------|-------|-------|-------|-------|
| TASA1 | 100 (%) | 72    | 73    | 72    | 98    | 68    | 35    |
| TASA2 | 72      | 100   | 68    | 67    | 65    | 61    | 32    |

F. Complementation and Inhibition Test

1. Construction of ASA2 cDNA in an Expression Vector

The tobacco ASA2 cDNA, from $Ser_{61}$ to the translation stop codon, has been amplified using primer 4 (SEQ ID NO: 6) and primer 5 (SEQ ID NO. 7) containing BamHI and KpnI overhangs, respectively. An expression vector (pQE30 from Qiagen) and the PCR fragment were digested with BamHI and KpnI and ligated in frame as confirmed by sequencing. This construct was named pQES61K.

2. Complementation and Inhibition Tests

Figure 5:
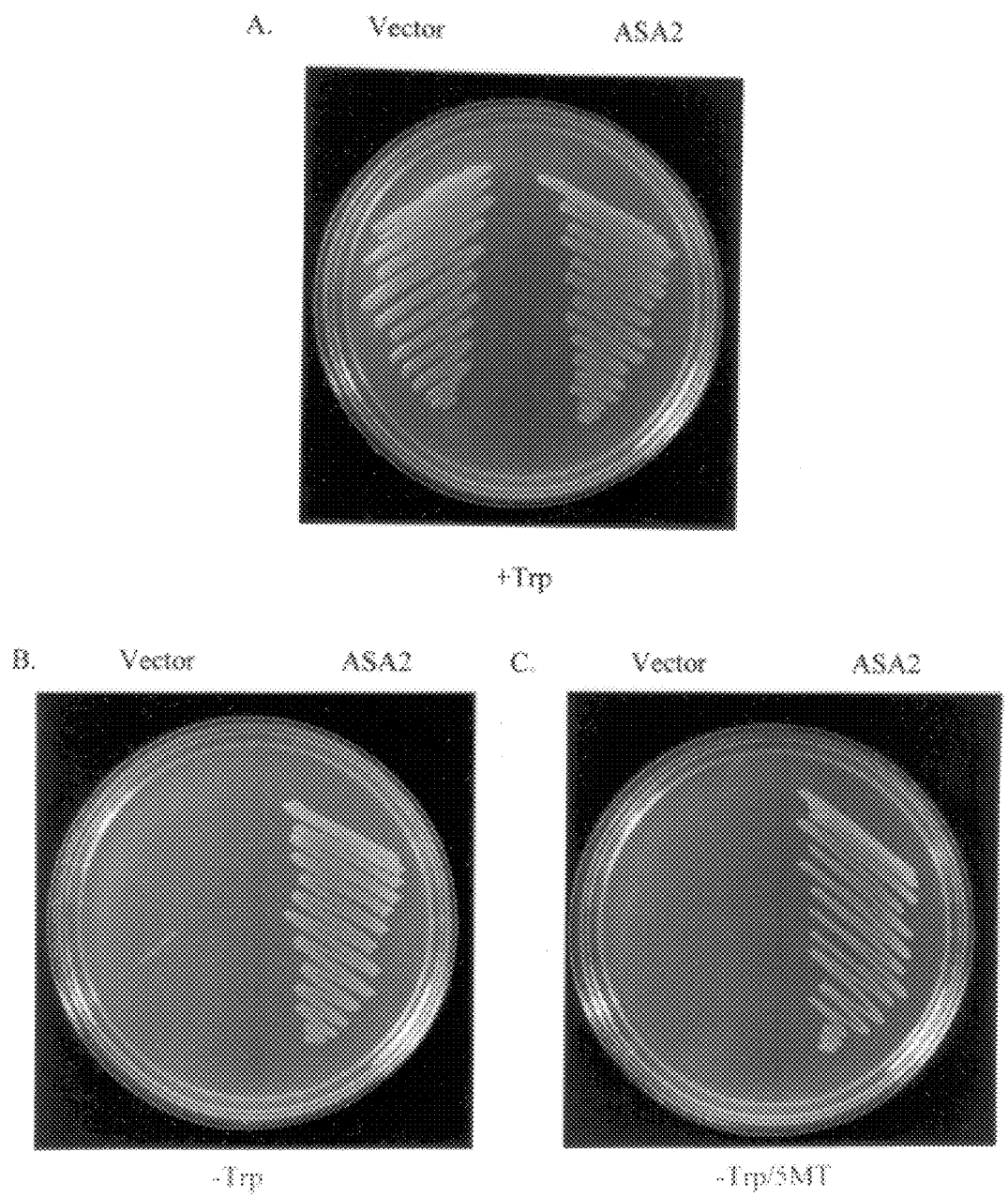
FIGS. 5A to 5C show photographs of complementation and inhibition tests.

FIG. 5 shows a picture of complementation and inhibition test. The pQES61K was transformed into a trpE nonsense (trpE 5972) mutant E. coli. The trpE nonsense mutant E. coli (trpE 5972) transformed with an expression vector itself (Vector) and the ASA2 cDNA ligated into the expression vector (ASA2) were plated on the M9 minimal medium containing isopropyl-thiogalactoside (IPTG, 0.1 mM) and ampicillin (100 μg/ml) and either with Trp (+Trp, FIG. 5A) or without Trp (–Trp, FIG. 5B). The complemented strain grew well on M9 medium without Trp and also with 300 μM 5MT (FIG. 5C) which inhibits the growth of the complemented strain carrying feedback-sensitive plant AS (Bohlmann et al., *Plant Physiol.*, 111: 507–514, 1996). The complementation and inhibition tests suggest that the ASA2 cDNA produces a functional enzyme which is resistant to high concentrations of 5MT. These results support the conclusion that the ASA2 gene is encoding a feedback-insensitive AS enzyme and can be used as a selectable marker. Complementation for the Trp requirement was also obtained with the E. coli deletion mutant (ΔtrpE 5390: Leu- and Trp-), which showed the same result as above (data not shown).

this and lower concentrations of Trp. This shows that the ASA2 cDNA does encode an AS α-subunit that is feedback-insensitive.

EXAMPLE 3

Construction of ASA2 Promoter-GUS Constructs

A. Cloning of the N. tabacum ASA2 Promoter

Figure 7:
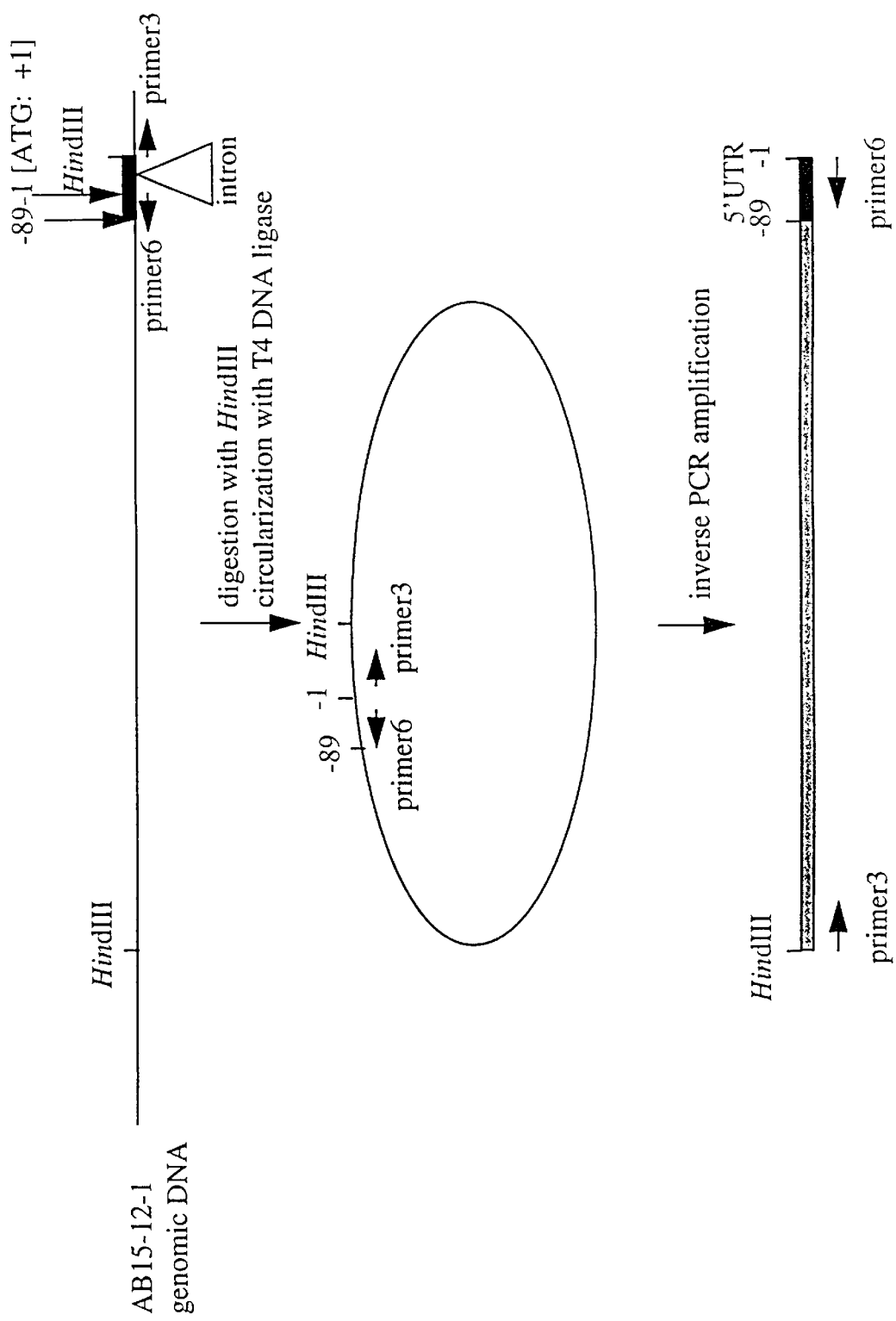
FIG. 7 shows a diagram of the strategy used to isolate the ASA2 promoter DNA sequence.

The promoter of the N. tabacum ASA2 gene was isolated using inverse PCR. FIG. 7 shows a diagram of the strategy used to isolate the ASA2 promoter. The HindIII digested AB15-12-1 genomic DNA was circularized with T4 DNA ligase and used as a template for inverse PCR with primer 3 (SEQ ID NO: 3) and primer 6 (SEQ ID NO: 8). These two primers were designed based on the sequence of the full-length ASA2 cDNA in Example 2 (SEQ ID NO: 4). The thermocycling program was as follows: denaturation at 95° C. for 1 min., annealing at 50° C. for 1 min., and extension at 72° C. for 2 min for 30 cycles. There was an initial 5 min. denaturation at 95° C. prior to beginning the thermocycling program above. Upon completion of the thermocycling program, there was an extension at 72° C. for 10 min. An approximately 2.3 kb fragment strongly hybridized to the full-length ASA2 cDNA clone from Example 2. This was expected since there was a 90 bp overlap between the inverse PCR fragment and the 5' end of the ASA2 cDNA. The sequencing results showed a perfect match in this overlapping region.

B. Construction of ASA2 Promoter-GUS Constructs

Figure 8:
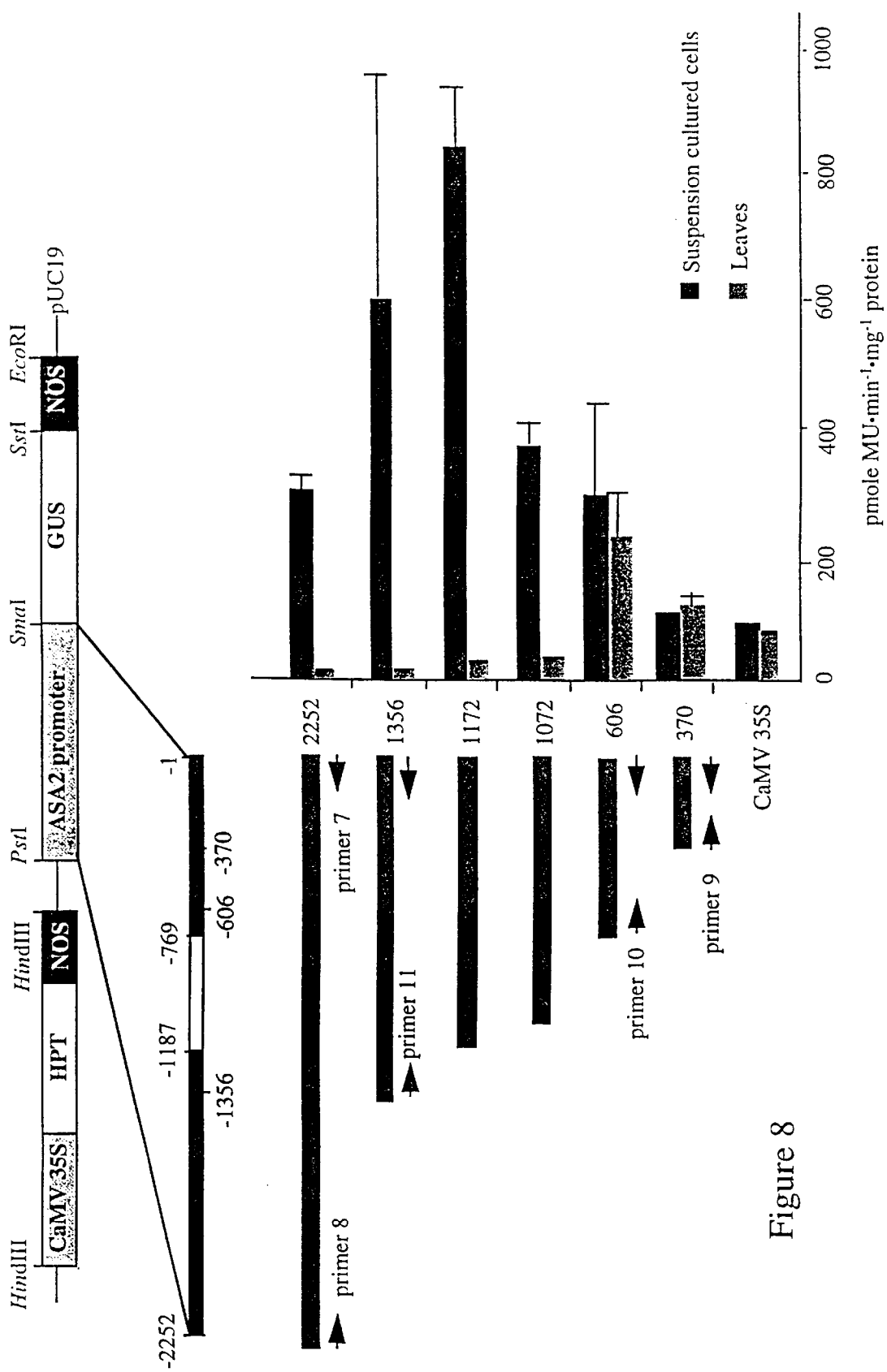
FIG. 8 describes the construction of the ASA2 promoter—GUS reporter gene constructs, and the subsequent deletion analysis of the ASA2 promoter.

FIG. 8 describes the construction of the ASA2 promoter-beta-glucuronidase reporter gene constructs, and the subsequent deletion analysis of the ASA2 promoter. Beta-glucuronidase is abbreviated as GUS. The pBI221 (Clontech- Catalog#6019-1, Palo Alto, Calif.) vector was used to provide the GUS reporter gene and NOS3' terminator. "NOS" denotes nopaline synthase terminator. A database search (Find Pattern program for transcription factors) obtained using the Wisconsin Package from the Genetics Computer Group, Inc. (575 Science Dr., Madison, Wis.) showed that there were eight possible TATA boxes in the 2,297 bp fragment. BLAST analysis showed that nucleotide sequences between −769 and −1,187 exhibited 81% identity to the promoter region of the N. tabacum plant defense-related str246C gene (Froissard et al., Plant Mol. Biol. 26(1): 515–521, 1994) and part of the coding region of organ-specific and auxin-inducible tobacco parA-related gene (Genbank accession number: D42119). Based on these database search results, deletion was performed by using PCR amplification with four sets of primers.

Each primer contained a restriction enzyme site overhang for cloning. Primer 7 (SEQ ID NO: 9) contains the SmaI site. Primers 8 (SEQ ID NO: 10), 9 (SEQ ID NO: 11), 10 (SEQ ID NO: 12), and 11 (SEQ ID NO: 13) contain the PstI site. The four sets of primers: primers 7 (SEQ ID NO: 9) and 8 (SEQ ID NO: 10); primers 7 (SEQ ID NO: 9) and 9 (SEQ ID NO: 11); primers 7 (SEQ ID NO: 9) and 10 (SEQ ID NO: 12); and primers 7 (SEQ ID NO: 9) and 11 (SEQ ID NO: 13), amplified 2,252 bp, 370 bp, 606 bp, 1356 bp fragments, respectively. These four fragments were cloned into the pBI221 vector in place of the CaMV 35S promoter and were designated 2252, 370, 606, and 1356, respectively (FIG. 8). An additional construct was also prepared in which the hygromycin resistance selectable marker gene (hpt) was ligated into a HindIII site, so that expression of the hpt gene was controlled by the CaMV 35S promoter and the NOS3' terminator. All constructed plasmid DNAs were transformed into E. coli DH5α and stored at −70° C. with 15% glycerol.

The following describes another ASA2 Promoter-GUS construct. In this construct, the 5' end of the ASA2 promoter fragment (−1356 to −1) has additionally been deleted by using ExoIII nuclease and S1 mungbeam nuclease (Stratagene) to determine the specific region which controls tissue-specific expression. The deleted fragments, −1172 to −1 and −1072 to −1 were ligated into pBI221 replacing the CaMV 35S promoter between the HindIII and SmaI sites, designated 1172 and 1072, and GUS expression was determined.

C. Sequence Analysis

The full-length ASA2 promoter was sequenced using standard sequencing methods (Sanger Dideoxy) of the full-length promoter clone described in Example 3, section A. The sequencing results indicated that an approximately 2.3 kb fragment is the promoter region of the ASA2 gene (FIG. 9; SEQ ID NO: 14), since the sequence of a 89 bp overlapping region between the promoter fragment and 5' upstream of the translation start codon of the ASA2 cDNA (SEQ ID NO: 4) showed a perfect match. The −1 nucleotide position in FIG. 9 corresponds to the nucleotide sequence upstream of the translation start codon (ATG). There were eight possible TATA boxes (−121, −280, −432, −457, −566, −634, −1169, and −2031), one CAAT site (−730), and many transcriptional factor binding sites such as a Pu box (−61 to −66), PEA3 (−62 to −67), AP-1 (−697 to −703) as activator or enhancer motifs. Nucleotide sequences between −769 and −1,187 exhibited 81% identity to the promoter region of N. tabacum plant defense-related str246C gene (Froissard et al., 1994), and part of the coding region of the organ-specific and auxin-inducible tobacco parA-related gene (Genbank accession number: D42119). These results indicated that more than one transcript could possibly be transcribed by this promoter region. S1-nuclease assay by hybridizing the 372 bp (−1 to −372) promoter fragment as a single stranded probe against total RNA obtained from the AB15-12-1 tissue culture cells showed more than one band, which supports this conclusion (data not shown). This work will be continued to show clearly which sites are involved in transcription initiation.

D. Expression of the GUS Constructs

1. Transformation. The constructed plasmid DNAs were isolated by using a Plasmid Maxi Kit (Qiagen, catalog #12162, Chatsworth, Calif.) and transformed into tobacco suspension cells (AB15-12-1 cells) and leaves (from plants regenerated from the AB15-12-1 cell line) using a Particle Inflow Gun (PIG) (1 μg DNA and 0.5 mg of 1.0 μm diameter tungsten particles/shot at 80 psi). The sample was incubated at 24° C. (60 $\mu Em^{-2}s^{-1}$) for 3 days after transformation. The promoter activity was determined by GUS histochemical assay with 5-bromo-4-chloro-3-indoyl glucuronide (X-Gluc) as substrate and by fluorimetric MUG assay with 4-methylumbelliferyl β-D-glucuronide (Jefferson, R. A., Plant Mol. Biol. Reporter, 5: 387–405, 1987).

Two chimeric GUS constructs controlled by 2252 and CaMV 35S promoters in a binary vector (pBI101, Clontech) were stably transformed into tobacco plants using Agrobacterium tumefaciens, and GUS activity was determined with the transgenic tobacco plants.

2. Expression. Strong transient GUS gene expression controlled by the full-length ASA2 promoter started to appear within one hour of incubation with the substrate (X-Gluc) in tobacco suspension cells (AB15-12-1 cells) bombarded with this clone. Little expression was observed in leaves after 10 to 12 hours incubation. Transformed leaves were extracted with ethanol at 37° C. overnight. The level of GUS gene expression controlled by the CaMV 35S promoter showed no significant difference between cultured cells and leaves. These experiments were repeated and the GUS activity was quantitated by the fluorimetric MUG assay and similar results were obtained (FIG. 8). These results suggest that the ASA2 promoter controls tissue-specific gene expression which was also strongly supported by the results of the ASA2 gene expression at the mRNA level (FIG. 3). In addition, these data indicate that the promoter is very active in cultured cells, and following selection the plants that were regenerated would not express the selectable marker gene at an appreciable level.

Strong transient GUS gene expression in suspension cultured cells especially 5MT-resistant suspension cultured cells has been found in the chimeric GUS constructs 2252, 1356, 1172, and 1072, while comparably low expression has been detected in leaves. The promoter region between −606 to −1 produced similar GUS gene expression in suspension cultured cells and leaves. These results suggest that the region between −2252 to −606 is involved in a tissue-specific gene expression. Transgenic tobacco plants carrying 2252 did not show any GUS activities in most tissues except for restricted epidermal cells in the very young leaves (FIGS. 10A and 10B) and calli induced from the transgenic tobacco leaves, which also supports the hypothesis that the region between −2252 to −606 regulates tissue-specific expression.

E. Strong Constitutive Promoter (−606 to −1) in Dicotyledonous Plants

The transient and stable GUS expression controlled by the three ASA2 deleted promoters (2252, 1356, and 606) and the control promoter (the CaMV 35S promoter), were investigated in several dicotyledonous plants such as Chinese Milk Vetch, *D. innoxia, N. sylvestris*, peanut, potato, soybean, tomato, and a monocotyledonous plant such as wheat (Table 2). Different plant tissues of each plant were used for GUS expression, as follows: Leaves and suspension cultured cells of *D. innoxia*, roots of Chinese Milk Vetch, leaves and suspension cells (5MT$^s$) and (5MT$^r$) of *N. sylvestris*, embryonal axis of peanut, leaves of potato, embryogenic cells, leaves, and suspension cultured cells of soybean, leaves (wildtype and regenerant from 5MT$^r$ suspension cells), roots, stems, and suspension cells (5MT$^s$ and 5MT$^r$) of tobacco, leaves of tomato, and scutellum of wheat. The 606-GUS construct showed strong constitutive expression in most tissues of dicotyledonous plants. The 1356-GUS construct showed tissue-specific expression in tobacco and possibly *D. innoxia, N. sylvestris*, potato, and tomato which belong to the Solanaceae family, and weak expression in wheat similar to that of the CaMV 35S promoter.

TABLE 2

GUS activity controlled by the ASA2 and CaMV 35S promoters in 9 different plant species.

| Plants | Sources of plant tissues | GUS activity | | | |
|---|---|---|---|---|---|
| | | 606 | 1356 | 2252 | 35S |
| Chinese Milk Vetch | roots | nt | +++* | +* | +++* |
| D. innoxia | suspension cultured cells (SC) | +++ | nt | ++ | ++ |
| | leaves | ++ | very low | very low | ++ |
| N. sylvestris | 5MT$^s$ SC | ++ | low | low | ++ |
| | 5MT$^r$ SC | ++++++ | ++++++ | ++++ | +++ |
| | leaves (wild type) | +++ | low | low | ++ |
| Peanut | embryonal axis | ++ | ++++ | nt | + |
| Potato | leaves | ++ | + | + | ++ |
| Soybean | SC | ++++ | nt | + | + |
| | embryogenic cells | ++++ | ++ | nt | +++ |
| | leaves | ++++ | nt | ++ | + |
| Tobacco | 5MT$^s$ SC | ++ | + | + | ++ |
| | 5MT$^r$ SC | ++++ | ++++ | +++ | +++ |
| | leaves (wild type) | +++ | low | very low* | +++* |
| | regenerant leaves from 5MT$^r$ SC | +++ | very low | very low | ++ |
| | roots | nt | nt | —* | +++* |
| | stems | nt | nt | —* | +++* |
| Tomato | leaves | + | low | low | ++ |
| Wheat | scutellum | − | + | nt | + |

−: no expression,
+ to ++++++: weak to strong expression,
nt: not tested,
*GUS expression on transgenic plants transformed with different chimeric constructs using Agrobacterium.

EXAMPLE 4

Cloning of the *N. tabacum* ASA1 and ASA3 genes

A. Cloning Strategy

Figure 11:
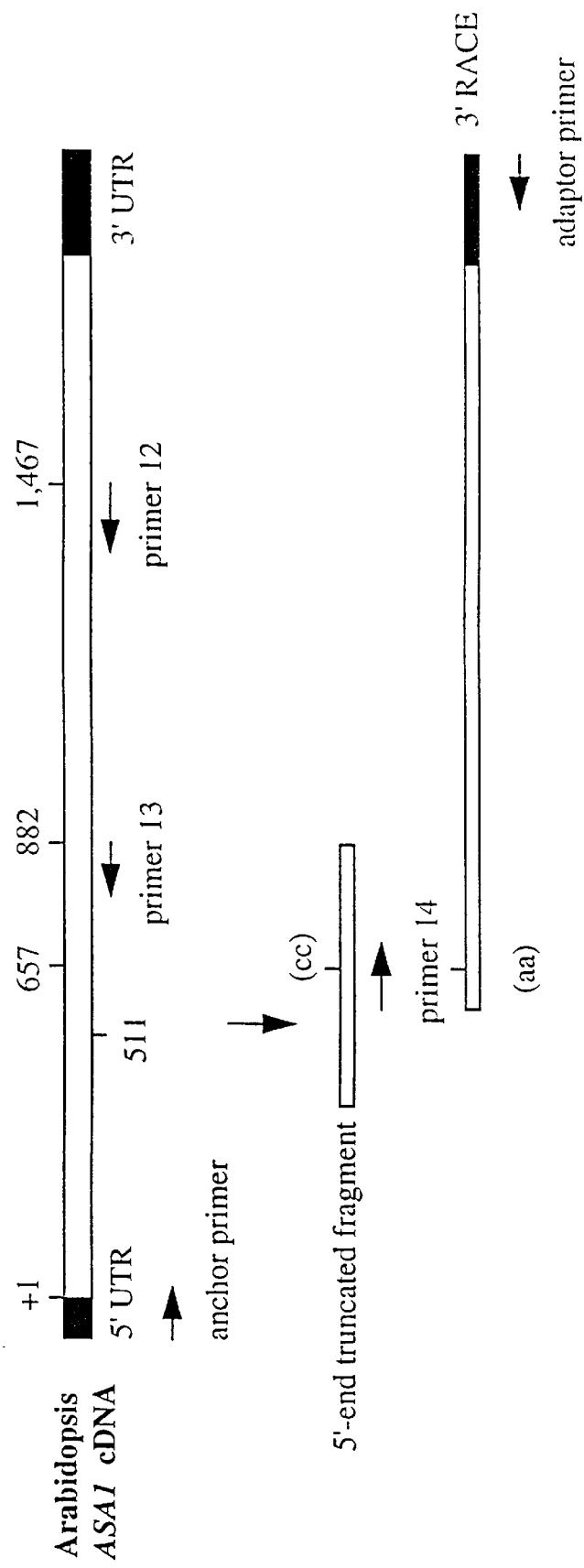
FIG. 11 shows a diagram of the A. thaliana ASA1 cDNA. The A. thaliana ASA1 cDNA sequence was used to design degenerate primers to clone the N. tabacum ASA1 gene (5' end truncated). The direction of the arrows, numbers, and black and white bars represent orientation of primers, nucleotide sequence of 5' end of primers, 5' and 3' UTR, and an overlapping region between the 5' and 3' clones, respectively.

The *N. tabacum* ASA1 cDNA (5' fragment), ASA1 cDNA (3' fragment), ASA1 genomic, and ASA3 partial genomic clones were obtained by using 5' and 3' RACE, genomic library screening, and PCR amplification, respectively. FIG. 11 shows a diagram of the *N. tabacum* ASA1 cDNA. The *A. thaliana* ASA1 cDNA amino acid sequence was used to construct heterologous primers to clone the *N. tabacum* ASA1 gene (5' end truncated). The *N. tabacum* ASA1 cDNA was also isolated by using 5' and 3' RACE. All procedures including the PCR reaction were exactly the same as those described for cloning the *N. tabacum* ASA2 gene (Example 2). The 5' end cDNA was isolated with degenerate primer 12 (SEQ ID NO: 15). The sequence of primer 12 was based upon the predicted amino acid sequence of the *A. thaliana* ASA1 gene. Primer 13 (SEQ ID NO: 16) was used for nested PCR to produce an approximately 0.6 kb 5' end truncated clone. Primer 14 (SEQ ID NO: 17) was used to isolate an approximately 1.4 kb fragment of the 3' end of the ASA1 cDNA clone. Both fragments were cloned into a commercially available pGEM-T vector (Promega) and sequenced by the Genetic Engineering Lab at the University of Illinois, using the Sanger Dideoxy sequencing method (SEQ ID NO: 24).

Figure 12:
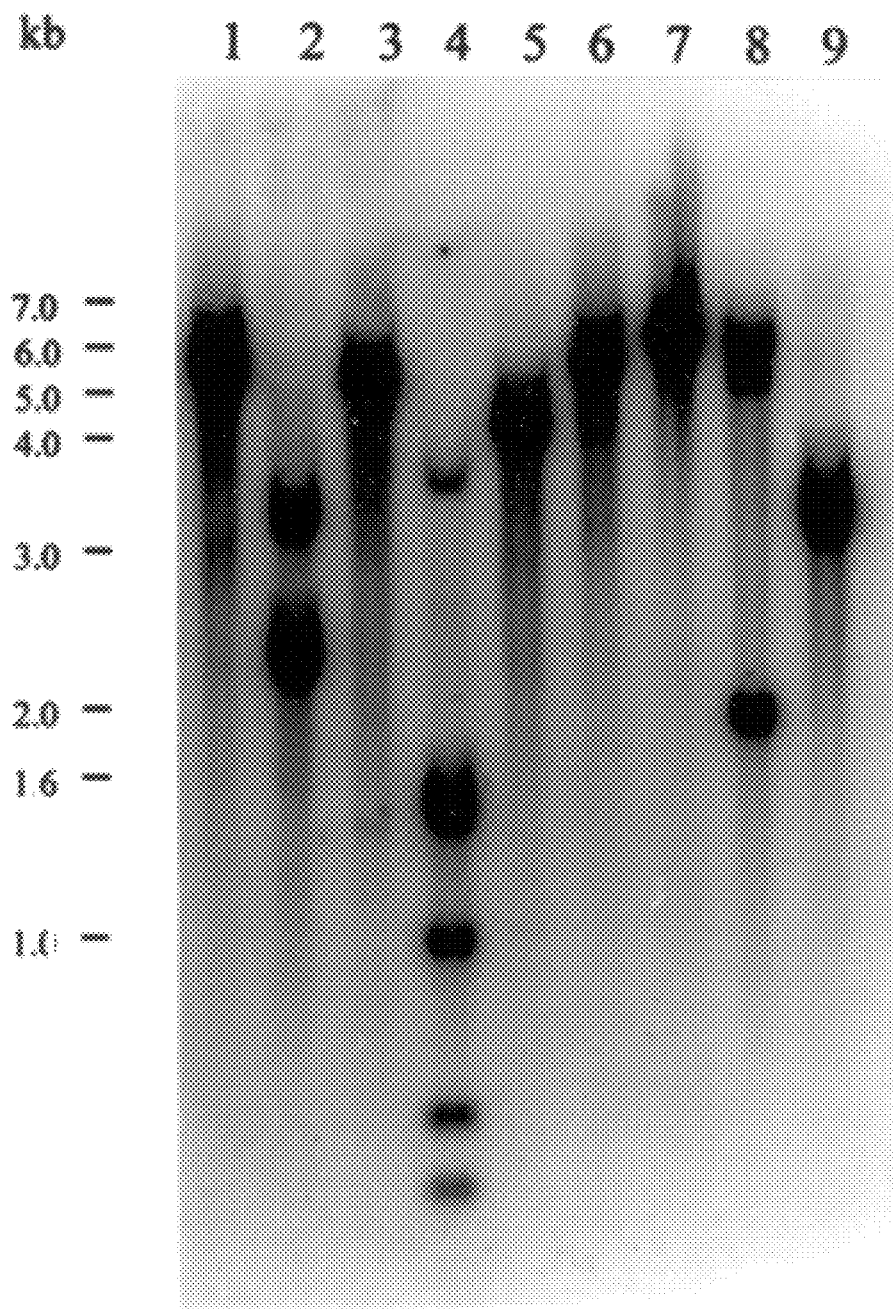
FIG. 12 is a Southern hybridization using a four kb PstI fragment of the ASA genomic clone as a probe to determine how many ASA genes exist in the tobacco genome.

The tobacco genomic ASA clone was obtained by screening a wildtype *N. tabacum* genomic library (Clontech, 5×10$^5$ pfu/ml -catalog #FL1071d, Palo Alto, Calif.). This genomic library screening was done before cloning the *N. tabacum* ASA2 gene, therefore, *A. thaliana* ASA1 and ASA2 cDNA clones were used as probes. A total of 18 positive colonies were selected. Only one colony seems to contain an AS gene which was supported by PCR amplification (data not shown). The *N. tabacum* ASA genomic clone (approximately 7 kb) was digested with SalI and cloned into pBluescript SK-. A four kb PstI fragment of the ASA genomic clone was used as a probe to determine how many ASA genes exist in the tobacco genome by using Southern hybridization (FIG. 12). Sequencing is in progress at the Molecular Analysis and Synthesis Section of The Samuel Roberts Noble Foundation, Inc. (2510 Sam Noble Parkway, Ardmore, Okla.), and this sequencing will be necessary to prove whether or not this clone is an ASA gene.

Figure 13:
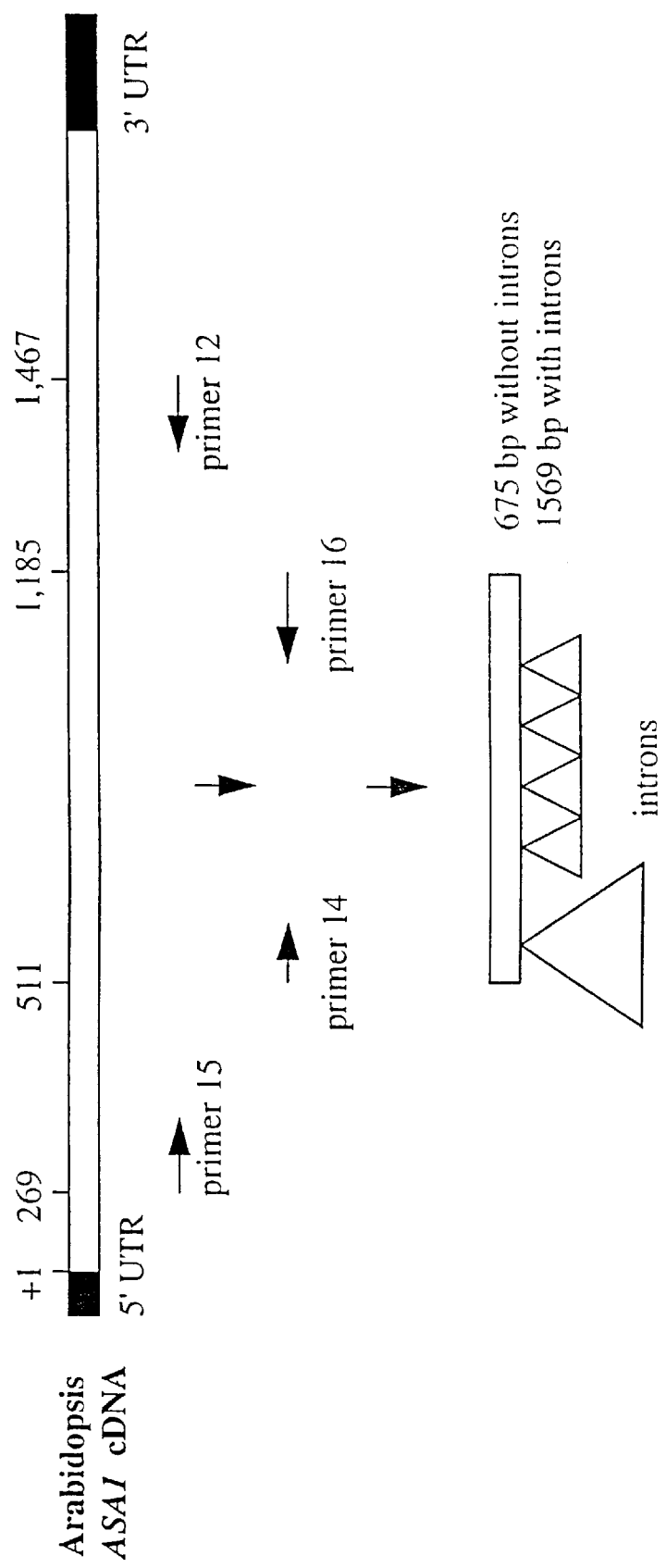
FIG. 13 shows the strategy for nested polymerase chain reaction (PCR) amplification to isolate tobacco partial genomic DNAs by PCR amplification with primer 15 (SEQ ID NO: 18) and primer 12 (SEQ ID NO: 15), primer 14 (SEQ ID NO: 17) and primer 16 (SEQ ID NO: 19). These degenerate primers were designed based on the amino acid sequence predicted from the nucleotide sequences of the A. thaliana ASA1 gene.

Tobacco partial genomic DNAS, with and without intron (s), were isolated by using PCR amplification with degenerated primers: primer 15 (SEQ ID NO: 18) and primer 12 (SEQ ID NO: 15), primer 14 (SEQ ID NO: 17) and primer 16 (SEQ ID NO: 19) for nested PCR (FIG. 13). These degenerated primers were designed based on the predicted amino acid and nucleotide sequences of the *A. thaliana* ASA1 gene, respectively.

Figure 14:
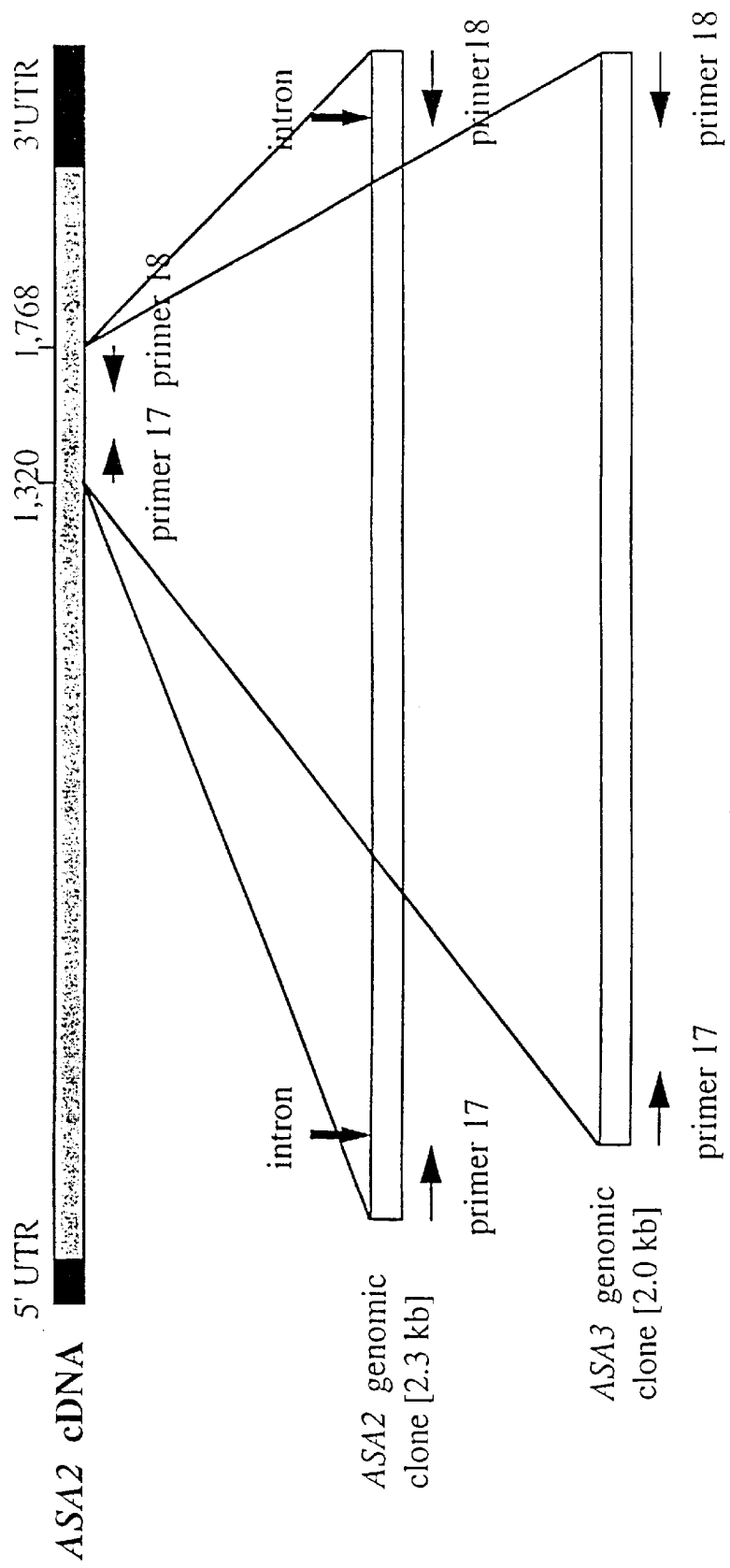
FIG. 14 shows the strategy of how N. tabacum ASA2 and ASA3 partial genomic clones were obtained by PCR amplification with primer 16 (SEQ ID NO: 19) and primer 17 (SEQ ID NO: 20) with AB15-12-1 genomic DNA as a template.

*N. tabacum* ASA2 and ASA3 partial genomic clones were obtained by PCR amplification with primer 17 (SEQ ID NO: 20) and primer 18 (SEQ ID NO: 21) with AB15-12-1 genomic DNA as a template (FIG. 14). The annealing temperature was 55° C. for 1 min. in 30 cycles. The final composition of the PCR reaction and the reaction conditions were the same as described in Example 2, section B. Two fragments (2.0 kb and 2.3 kb) were amplified that strongly hybridized to the ASA2 clone. These fragments were cloned into pGEM-T vector, and sequenced.

B. Sequence Analysis of the ASA Genes

We have isolated one 5' end truncated ASA1 cDNA, one ASA genomic, one full-length ASA2 cDNA, and one partial ASA3 genomic clones. These AS genes encode the α-subunit of AS in tobacco (ASA). we have also cloned AS genes without introns. Both ASA1 genes probably encode feedback-sensitive AS, but characteristics of both genes are different at the mRNA level such as size of transcript and tissue-specificity. The ASA genomic clone hybridized to a single band for most restriction enzyme digestions, which indicates that this ASA gene is different from the ASA1 cDNA clone (FIG. 12). Tobacco ASA1 cDNA showed 98% amino acid identity to *A. thaliana* ASA1. Even though tobacco and Arabidopsis are not closely related phylogenetically, we could isolate partial ASA1 cDNA and genomic clones with and without intron(s) from *N. sylvestris, N. tomentosiformis*, and *N. tabacum*, which showed almost 98% identity to Arabidopsis ASA1 (data not shown). Based on these results, the ASA1 gene is a more conserved AS gene among different plant families or orders than is the ASA2 gene.

The ASA2 gene may encode a feedback-insensitive AS based on gene expression at the mRNA level (FIG. 3), feedback inhibition characteristics (FIG. 6) of the gene product expressed in E. coli, and ASA2 promoter activity with GUS contructs (Example 3). ASA3 may be another ASA2-like gene which originated from the other parent, since N. tabacum is an allotetraploid between N. sylvestris and N. tomentosiformis. The partial sequence between the ASA2 and ASA3 genomic clones (ASA2G, ASA3G) showed approximately 85% (56 nucleotides mismatch out of 657) nucleotide identity to each other (FIGS. 15A and 15B). We need to complete cloning and sequencing of the rest of the ASA3 gene (SEQ ID NO: 22). It is possible that the size of both transcripts is very similar, since we found only one transcript size detected by the ASA2 cDNA clone. It is necessary to check Northern hybridization with the ASA3 clone as a probe to determine whether or not the ASA3 gene may also encode a feedback-insensitive AS that has a similar size of transcript to ASA2.

EXAMPLE 5

Use of the ASA2 Promoter to Drive Different Selectable Markers

A. Possible Expression Constructs

The 2.3 kb ASA2 promoter fragment (SEQ ID NO: 14) can be attached to many possible selectable markers including the ASA2 structual gene (SEQ ID NO: 4) that should impart resistance to 5MT, to the neomycin phosphotransferase II gene that should impart resistance to kanamycin, to the hygromycin phosphotransferase gene that should impart resistance to hygromycin and to the phosphinothricin-acetyl transferase gene that should impart resistance to phosphinothricin (Basta).

B. Transformation

Once the promoter and selectable marker gene with a suitable terminator sequence are assembled in a plasmid the construct can be used to transform plant cells using any of the possible transformation systems including particle bombardment of cells or tissues, electroporation of protoplasts or cells and Agrobacterium mediated transformation if the construct is placed into correct plasmid in the bacterium.

C. Utility of the ASA2 Promoter and ASA2 Structural Gene

The use of the ASA2 structural gene as a selectable marker would provide a new selectable marker for use in selecting transformed cells from the mass of untransformed cells. An effective selectable marker is required since the transformation process is relatively inefficient.

The use of the ASA2 promoter to drive any of the possible selectable markers should allow selection for the resistance marker in cultured cells, but not in the regenerated plant. This is because the promoter is very active in cultured cells (see Example 3, Section C), but following selection the plants that are regenerated will not express the selectable marker gene at an appreciable level. This lack of expression at the whole plant level will blunt any arguments that expression in the plants will cause environmental harm or that expression of the selectable marker gene will have a detrimental effect on the plant itself.

EXAMPLE 6

Expression of the N. tabacum ASA2 Promoter and ASA2 Structural Gene in Different Plant Species A. Expected Expression Patterns The N. tabacum ASA2 promoter and structural gene were isolated from the dicot N. tabacum, where the characteristics described of tissue culture specificity imparted by the promoter (see Example 3) and very clear resistance to 5MT imparted by the ASA2 structural gene (see Example 1) have been demonstrated. It is expected that the 5MT resistance carried by the structural gene would be expressed in other plant species (both monocot and dicot), since the AS genes are conserved and the alteration in the sequence should provide resistance. The expression characteristics of the promoter are less predictable.

B. Strategy for Construction of Vectors for Expression

To test the expression of the N. tabacum ASA2 promoter and structural gene in different plant species, we will use the following constructs to transform cell cultures of N. tabacum, carrot, D. innoxia and corn using the optimum transformation protocol for each plant species. The following constructs will be tested: (A) The ASA2 promoter driving the ASA2 gene (cDNA clone; A.T.C.C. Accession Number 209150), (B) the ASA2 promoter driving the npt II gene, (C) the CaMV 35S promoter driving the ASA2 structual gene, and (D) the CaMV 35S promoter driving the nptII gene as a control. Following DNA introduction, the transformed cells will be selected with the suitable agent and the selected transformed cells regenerated into plants. The expression of the selectable marker gene will be determined in the cultured cells and in the regenerated plants. Untransformed controls will be used for comparison. The expected results are shown in Table 3.

TABLE 3

| | Expected outcome | | | |
|---|---|---|---|---|
| | Resistance in Cells | | Expression in Plants | |
| Construct | 5MT | Kanamycin | ASA2 | nptII |
| A. ASA2 promoter-ASA2 | + | − | − | − |
| B. ASA2 promoter-nptII | − | + | − | − |
| C. CaMV35S-ASA2 | + | − | + | − |
| D. CaMV35S-nptII | − | + | − | + |
| untransformed control | − | − | − | − |

C. Construction of the ASA2 Promoter Fused to ASA2 cDNA

The ASA2 cDNA from ATG [+1] codon to +2072 including 3' UTR was amplified with primers containing SmaI site at 5' (primer 19, SEQ ID NO: 26) and EcoRI site at 3' (primer 20, SEQ ID NO: 27). Both chimeric construct plasmids, ASA2 promoter-GUS, and the ASA2 cDNA PCR product were digested with both SmaI and EcoRI. The ASA2 cDNA fragment was inserted in place of the fragment containing a GUS gene and NOS 3' terminator in the chimeric construct plasmids with the different sizes of the deleted ASA2 promoters. The construct such as CaMV 35S promoter-ASA2, was constructed using the same method as above. In order to fuse other selectable marker genes into the ASA2 promoter, the selectable marker gene including terminator was amplified with primers containing restriction enzyme sites which do not exist in promoter, gene, or terminator sequences. The PCR fragment can be ligated downstream of the ASA2 promoter. These constructs can be transformed by either using Agrobacterium, a biolistic bombardment, or protoplasts electroporation as described above.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

EXAMPLE 7

Determination of Amino Acid Residues Involved in Feedback Inhibition

Several regions of the AS amino acid sequence have been shown to affect feedback inhibition (Bohlmann et al., 1996, supra; Kreps, et al., 1996, supra; and Li & Last, 1996, supra). In the tobacco ASA2 of the present patent application, two amino acids, $Phe_{107}$ and $Arg_{108}$ in the same region as that found in *Ruta graveolens* ASα1 ($Arg_{138}$ for $Gln_{138}$, based on ASα1 amino acid sequence) are shown to be different from those in feedback-sensitive AS which are $Ser_{107}$ and $Gln_{108}$. To determine if $Phe_{107}$ and $Arg_{108}$ residues cause feedback insensitivity, the following site-directed mutagenesis was performed by changing the $Phe_{107}$ and $Arg_{108}$ residues to $Ser_{107}$ and $Gln_{108}$ as found in feedback-sensitive AS.

Site-Directed Mutagenesis and Complementation/Inhibition Tests

Site-directed mutagenesis was performed by PCR using a primer containing mismatch nucleotide sequences by changing four of the original nucleotides (CCTGGTTTTCGA) to (CCCGGGTCTCAA). The first two mismatch nucleotides do not change the amino acid codon, $Pro_{105}$ and $Gly_{106}$ but create a SmaI site. The last two mismatch nucleotides change $Phe_{107}$ and $Arg_{108}$ to $Ser_{107}$ and $Gln_{108}$. Two PCR products were obtained using primers identified as SEQ ID NO. 28 (5'-ACTAGT GGATCCTGCCTTCACTCTTCATCTCTAG-3', BamHI overhang) and SEQ ID NO. 29 (5'-ACCTTGAGA CCCGGGTTCAACGGATTCAAAGAGAAAGCTTGG-3', SmaI overhang); and SEQ ID NO. 30 (5'-TCCGTTGAA CCCGGGTCTCAAGGTTCTAGTGTTGGTCGCTAC-3', SmaI overhang), and SEQ ID NO. 31 (5'-TTGCGG GGTACCCTAGTTTCTTTTCTCATGTAC-3', KpnI overhang). These two PCR fragments were ligated followed by SmaI digestion and then ligated in frame into the pQE30 vector after double digestion with BamHI and KpnI.

Figure 16:
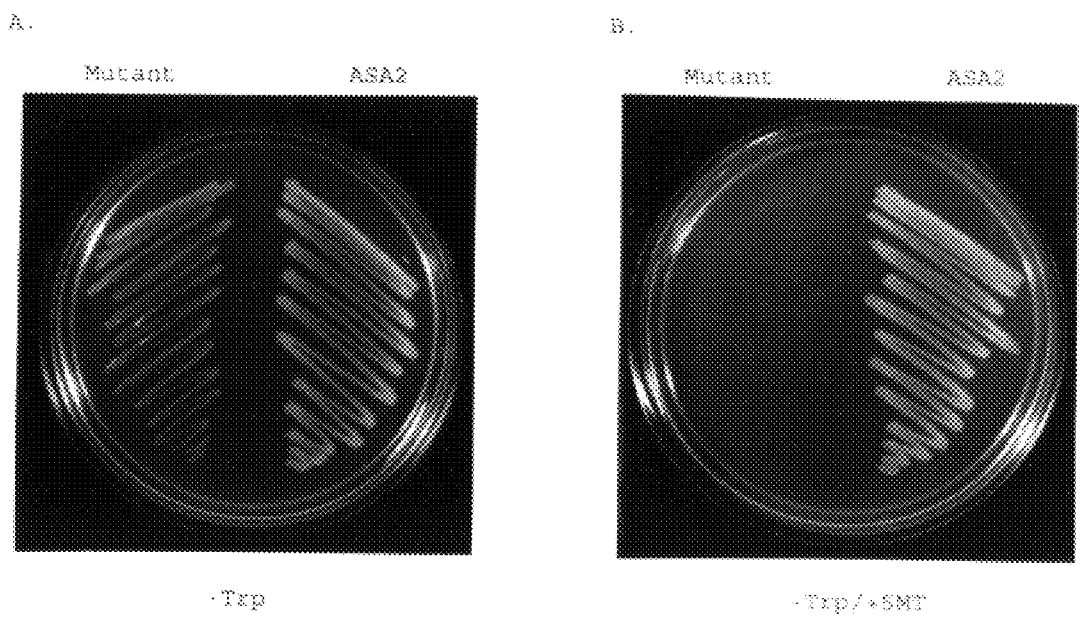
FIG. 16 shows the complementation of E. coli trpE5972 by the tobacco ASA2 and its site-directed mutants which were plated onto M9 minimal medium containing ampicillin (100 μg/ml) and isopropylthiogalactoside (0.1 mM) without 300 μM 5MT (FIG. 16A) and with 300 μM 5MT (FIG. 16B).

The chimeric constructs were transformed into trpE mutant *E. coli* (trpE5972, nonsense mutant) using $CaCl_2$ transformation (Sambrook et al., 1989, supra). Complemented strains were plated on M9 minimal medium containing ampicillin (100 μg/ml) and isopropylthiogalactoside (IPTG, 0.1 mM), but no Trp. For the inhibition test, 300 μM 5MT was added to the minimal medium described previously. FIGS. 16A and 16B were taken two days after streaking.

Results of Complementation and Inhibition Tests

The *E. coli* trpE5972 nonsense mutant transformed with the tobacco ASA2 cDNA and site-directed mutant ($Phe_{107}$, $Arg_{108}$ changed to $Ser_{107}$, $Gln_{108}$) both grew on minimal medium containing ampicillin and IPTG but no Trp (FIG. 16A). However, the complemented strain transformed with the site-directed mutant did not grow on the 300 μM 5MT-containing minimal medium without adding Trp (FIG. 16B), while the growth of the strain transformed with the ASA2 cDNA was not inhibited by 300 μM 5MT.

The results presented here support the conclusion that the ASA2 cDNA encodes the α-subunit of a feedback-insensitive AS in tobacco and the $Phe_{107}$ and $Arg_{108}$ residues are especially important in the control of feedback inhibition.

Deposit of Strains

The following cell line and clones were deposited under at the American Type Culture Collection, 12301 Parklawn Drive, Rockville, Md. 20852 according to the terms of the Budapest Treaty and will be maintained for a period of thiry (30) years from the date of deposit, or for five (5) years after the last request for the deposit, whichever is longer.

The *N. tabacum* AB-15-12-1 cell line maintained in MX medium containing 300 μM 5MT were deposited on Jul. 22, 1997, and accorded A.T.C.C. deposit number 209176.

The *N. tabacum* ASA2 promoter (as plasmid DNA pUCASA2-GUS and accorded A.T.C.C. deposit number 209150), *N. tabacum* ASA3 partial genomic clone (as plasmid DNA pGemTASA3 and accorded A.T.C.C. deposit number 209151), and *N. tabacum* ASA2 cDNA clone (as plasmid DNA pGemTASA2 and accorded A.T.C.C. deposit number 209152) were deposited on Jul. 22, 1997.

Availability of the deposited recombinant transfer vector is not to be construed as a license to practice the invention in contravention of the rights granted under the authority of any government in accordance with its patent laws.

The deposits and any other deposited material described herein are provided for convenience only, and are not required to practice the present invention in view of the teachings provided herein.

Also, the present invention is not to be considered limited in scope by the deposited recombinant transfer vector, since the deposited vector is intended only to be illustrative of particular aspects of the invention. Any recombinant transfer vector which can be used to prepare recombinant microorganism which can function to produce a recombinant protein product described herein is considered to be within the scope of this invention. Further, various modifications of the invention in addition to those shown and described herein which are apparent to those skilled in the art from the preceding description are considered to fall within the scope of the appended claims.

We claim:

1. A promoter having a nucleotide sequence selected from the group consisting of a nucleotide sequence according to SEQ ID NO: 14 and a fragment of SEQ ID NO: 14 which is capable of directing the transcription of a downstream structural gene in a plant cell.

2. The promoter of claim 1, wherein the fragment has a nucleotide sequence selected from the group consisting of nucleotide sequences from: position −1 to position −151; position −1 to position −214; position −1 to position −370; position −1 to position −606; position −1 to position −1356; and position −1 to position −2252 of SEQ ID NO: 14.

3. The promoter of claim 1, wherein said fragment is capable of directing constitutive transcription of a downstream structural gene in plant cells and whole plant tissues.

4. The promoter of claim 1, wherein said fragment is capable of directing a higher level of tissue specific transcription of a downstream structural gene in cells cultured from a plant transformed by the promoter, than in the transformed plant.

5. A nucleotide sequence selected from the group consisting of:

SEQ ID NOs: 24, 4, 22, 14, and 25.

6. A DNA construct comprising an expression cassette, which construct comprises, in the 5' to 3' direction, a promoter according to claim 1 and a structural gene positioned downstream from said promoter and operatively associated therewith.

7. The DNA construct of claim 6, wherein the structural gene encodes a protein selected from the group consisting of: ASA1, ASA2, and ASA3.

8. The DNA construct of claim 6, wherein the structural gene is not associated with the promoter in nature.

9. The DNA construct of claim 8, wherein the structural gene is selected from the group consisting of: *Phaseolus vulgaris* Ch 18, *Bacillus thuringiensis* cry1AC, *Vigna aconitifolia* P5CS, and csr1-1.

10. A transformed cell containing the DNA construct of claim 6.

11. A transformed plant comprising transformed plant cells containing a DNA of claim 6.

* * * * *

SEQUENCE LISTING

```
<160> NUMBER OF SEQ ID NOS: 31

<210> SEQ ID NO 1
<211> LENGTH: 21
<212> TYPE: DNA (cDNA)
<213> ORGANISM: Nicotiana tabacum

<400> SEQUENCE: 1
```

```
           gcggctttgt tctggcactc a                                      21

<210> SEQ ID NO 2
<211> LENGTH: 21
<212> TYPE: DNA (cDNA)
<213> ORGANISM: Nicotiana tabacum

<400> SEQUENCE: 2
ctgcaaatgt tcgccgctca a                                      21

<210> SEQ ID NO 3
<211> LENGTH: 21
<212> TYPE: DNA (cDNA)
<213> ORGANISM: Nicotiana tabacum

<400> SEQUENCE: 3
ctagttatgg atgaggacag g                                      21

<210> SEQ ID NO 4
<211> LENGTH: 2161
<212> TYPE: DNA (cDNA)
<213> ORGANISM: Nicotiana tabacum

<400> SEQUENCE: 4
gtcaaaaatc cccatttcac cgtttcctcg tttctcctcc tcactaattt tgtctctttc       60
tcttggtttg ctattgtgct cttgtaggaa tgcagtcgtt acctatctca taccggttgt      120
ttccggccac ccaccggaaa gttctgccat tcgccgtcat ttctagccgg agctcaactt      180
ctgcacttgc gcttcgtgtc cgtacactac aatgccgctg ccttcactct tcatctctag      240
ttatggatga ggacaggttc attgaagctt ctaaaagcgg gaacttgatt ccgctgcaca      300
aaaccatttt ttctgatcat ctgactccgg tgctggctta ccgtgtttg gtgaaagaag       360 acgaccgtga agctccaagc tttctctttg aatccgttga acctggtttt cgaggttcta      420
gtgttggtcg ctacagcgtg gtgggggctc aaccatctat ggaaattgtg gctaaggaac      480
acaatgtgac tatattggac caccacactg gaaaattgac ccagaagact gtccaagatc      540
ccatgacgat tccgaggagt atttctgagg gatggaagcc cagactcatt gatgaacttc      600
ctgataccct ttgtggtgga tgggttggtt atttctcata tgacacagtt cggtatgtag      660
agaacaggaa gttgccattc ctaagggctc agaggatga ccggaacctt gcagatattc       720
aattaggact atacgaagat gtcattgtgt ttgatcatgt tgagaagaaa gcacatgtga      780
ttcactgggt gcagttggat cagtattcat ctcttcctga ggcatatctt gatgggaaga      840
aacgcttgga atatattgtg tctagagtac aaggaattga gtctccaagg ttatctcccg      900
gttctgtgga tttctgtact catgcttttg gaccttcatt aaccaaggga acatgacaa       960 gtgaggagta caagaatgct gtcttacaag caaaggagca cattgctgca ggagacatat     1020
ttcaaatcgt tttaagtcaa cgctttgaga gagaacatt tgctgaccca tttgaagtgt      1080
acagagcatt aagaattgtg aatccaagcc catatatgac ttacatacaa gccagaggct     1140
gtattttagt tgcatcgagc ccagaaattt tgacacgtgt gaagaagaga agaattgtta     1200
atcgaccact ggctgggaca agcagaagag gaagacacc tgatgaggat gtgatgttgg      1260
aaatgcagat gttaaaagat gagaaacaac gcgcagagca catcatgctg gttgatttag     1320
gacgaaatga tgtaggaaag gtgtcaaaac ctggttctgt gaatgtcgaa aagctcatga     1380
gcgttgagcg gtattcccat gtgatgcaca taagctccac ggtctctgga gagttgcttg     1440
atcatttaac ctgttgggat gcactacgtg ctgcattgcc tgttgggacc gtcagtggag     1500
```

-continued

```
caccaaaggt aaaggccatg gagttgattg atcagctaga agtagctcgg agagggcctt   1560
acagtggtgg gtttggaggc atttcctttt caggtgacat ggacatcgca ctagctctaa   1620
ggacgatggt attcctcaat ggagctcgtt atgacacaat gtattcatat acagatgcca   1680
gcaagcgtca ggaatgggtt gctcatctcc aatccggggc tggaattgtg gctgatagta   1740
atcctgatga ggaacagata gaatgcgaga ataaagtagc cggtctgtgc cgagccattg   1800
acttggccga gtcagctttt gtaaagggaa gacacaaacc gtcagtcaag ataaatggtt   1860
ctgtgccaaa tctattttca agggtacaac gtcaaacatc tgttatgtcg aaggacagag   1920
tacatgagaa aagaaactag cgaatatgaa gatgtacata aattctaaag tggttttctt   1980
gttcagttta atcttttact ggattgagac tgtagttgct gaagatagtt gtttagaatg   2040
accttcattt tggtgttcct gaaaggacag tgcacatata tagcaaattg atcaaatgtt   2100
taatccttgt atgcgggtga gaatcaatgc catcagcaat ttggaaaaaa aaaaaaaaaa   2160
a                                                                    2161
```

```

<210> SEQ ID NO 5
<211> LENGTH: 616
<212> TYPE: PRT
<213> ORGANISM: Nicotiana tabacum

<400> SEQUENCE: 5

Met Gln Ser Leu Pro Ile Ser Tyr Arg Leu Phe Pro Ala Thr His Arg
  1               5                  10                  15

Lys Val Leu Pro Phe Ala Val Ile Ser Ser Arg Ser Ser Thr Ser Ala
             20                  25                  30

Leu Ala Leu Arg Val Arg Thr Leu Gln Cys Arg Cys Leu His Ser Ser
         35                  40                  45

Ser Leu Val Met Asp Glu Asp Arg Phe Ile Glu Ala Ser Lys Ser Gly
     50                  55                  60

Asn Leu Ile Pro Leu His Lys Thr Ile Phe Ser Asp His Leu Thr Pro
 65                  70                  75                  80

Val Leu Ala Tyr Arg Cys Leu Val Lys Glu Asp Asp Arg Glu Ala Pro
                 85                  90                  95

Ser Phe Leu Phe Glu Ser Val Glu Pro Gly Phe Arg Gly Ser Ser Val
            100                 105                 110

Gly Arg Tyr Ser Val Val Gly Ala Gln Pro Ser Met Glu Ile Val Ala
        115                 120                 125

Lys Glu His Asn Val Thr Ile Leu Asp His His Thr Gly Lys Leu Thr
    130                 135                 140

Gln Lys Thr Val Gln Asp Pro Met Thr Ile Pro Arg Ser Ile Ser Glu
145                 150                 155                 160

Gly Trp Lys Pro Arg Leu Ile Asp Glu Leu Pro Asp Thr Phe Cys Gly
                165                 170                 175

Gly Trp Val Gly Tyr Phe Ser Tyr Asp Thr Val Arg Tyr Val Glu Asn
            180                 185                 190

Arg Lys Leu Pro Phe Leu Arg Ala Pro Glu Asp Asp Arg Asn Leu Ala
        195                 200                 205

Asp Ile Gln Leu Gly Leu Tyr Glu Asp Val Ile Val Phe Asp His Val
    210                 215                 220

Glu Lys Lys Ala His Val Ile His Trp Val Gln Leu Asp Gln Tyr Ser
225                 230                 235                 240

Ser Leu Pro Glu Ala Tyr Leu Asp Gly Lys Lys Arg Leu Glu Ile Leu
                245                 250                 255
```

Val Ser Arg Val Gln Gly Ile Glu Ser Pro Arg Leu Ser Pro Gly Ser
            260                 265                 270

Val Asp Phe Cys Thr His Ala Phe Gly Pro Ser Leu Thr Lys Gly Asn
            275                 280                 285

Met Thr Ser Glu Glu Tyr Lys Asn Ala Val Leu Gln Ala Lys Glu His
            290                 295                 300

Ile Ala Ala Gly Asp Ile Phe Gln Ile Val Leu Ser Gln Arg Phe Glu
305                 310                 315                 320

Arg Arg Thr Phe Ala Asp Pro Phe Glu Val Tyr Arg Ala Leu Arg Ile
                325                 330                 335

Val Asn Pro Ser Pro Tyr Met Thr Tyr Ile Gln Ala Arg Gly Cys Ile
                340                 345                 350

Leu Val Ala Ser Ser Pro Glu Ile Leu Thr Arg Val Lys Lys Arg Arg
                355                 360                 365

Ile Val Asn Arg Pro Leu Ala Gly Thr Ser Arg Arg Gly Lys Thr Pro
                370                 375                 380

Asp Glu Asp Val Met Leu Glu Met Gln Met Leu Lys Asp Glu Lys Gln
385                 390                 395                 400

Arg Ala Glu His Ile Met Leu Val Asp Leu Gly Arg Asn Asp Val Gly
                405                 410                 415

Lys Val Ser Lys Pro Gly Ser Val Asn Val Glu Lys Leu Met Ser Val
                420                 425                 430

Glu Arg Tyr Ser His Val Met His Ile Ser Ser Thr Val Ser Gly Glu
                435                 440                 445

Leu Leu Asp His Leu Thr Cys Trp Asp Ala Leu Arg Ala Ala Leu Pro
                450                 455                 460

Val Gly Thr Val Ser Gly Ala Pro Lys Val Lys Ala Met Glu Leu Ile
465                 470                 475                 480

Asp Gln Leu Glu Val Ala Arg Arg Gly Pro Tyr Ser Gly Gly Phe Gly
                485                 490                 495

Gly Ile Ser Phe Ser Gly Asp Met Asp Ile Ala Leu Ala Leu Arg Thr
                500                 505                 510

Met Val Phe Leu Asn Gly Ala Arg Tyr Asp Thr Met Tyr Ser Tyr Thr
                515                 520                 525

Asp Ala Ser Lys Arg Gln Glu Trp Val Ala His Leu Gln Ser Gly Ala
                530                 535                 540

Gly Ile Val Ala Asp Ser Asn Pro Asp Glu Glu Gln Ile Glu Cys Glu
545                 550                 555                 560

Asn Lys Val Ala Gly Leu Cys Arg Ala Ile Asp Leu Ala Glu Ser Ala
                565                 570                 575

Phe Val Lys Gly Arg His Lys Pro Ser Val Lys Ile Asn Gly Ser Val
                580                 585                 590

Pro Asn Leu Phe Ser Arg Val Gln Arg Gln Thr Ser Val Met Ser Lys
                595                 600                 605

Asp Arg Val His Glu Lys Arg Asn
            610                 615

<210> SEQ ID NO 6
<211> LENGTH: 30
<212> TYPE: DNA (genomic)
<213> ORGANISM: Nicotiana tabacum

<400> SEQUENCE: 6
actagtggat cctctaaaag cgggaacttg                                30

```
<210> SEQ ID NO 7
<211> LENGTH: 33
<212> TYPE: DNA (genomic)
<213> ORGANISM: Nicotiana tabacum

<400> SEQUENCE: 7
ttgcggggta ccctagtttc ttttctcatg tac                              33

<210> SEQ ID NO 8
<211> LENGTH: 21
<212> TYPE: DNA (cDNA)
<213> ORGANISM: Nicotiana tabacum

<400> SEQUENCE: 8
acgactgcat tcctacaaga g                                           21

<210> SEQ ID NO 9
<211> LENGTH: 30
<212> TYPE: DNA (cDNA)
<213> ORGANISM: Nicotiana tabacum

<400> SEQUENCE: 9 ggatccccg ggtcctacaa gagcacaata                                   30

<210> SEQ ID NO 10
<211> LENGTH: 30
<212> TYPE: DNA (cDNA)
<213> ORGANISM: Nicotiana tabacum

<400> SEQUENCE: 10
gcatgcctgc agcaaatcta ttcgatagtg                                  30

<210> SEQ ID NO 11
<211> LENGTH: 30
<212> TYPE: DNA (cDNA)
<213> ORGANISM: Nicotiana tabacum

<400> SEQUENCE: 11
gcatgcctgc agtcagccaa atgtgtccaa                                  30

<210> SEQ ID NO 12
<211> LENGTH: 30
<212> TYPE: DNA (cDNA)
<213> ORGANISM: Nicotiana tabacum

<400> SEQUENCE: 12
gcatgcctgc agtgtattgc ccatttcatt                                  30

<210> SEQ ID NO 13
<211> LENGTH: 30
<212> TYPE: DNA (cDNA)
<213> ORGANISM: Nicotiana tabacum

<400> SEQUENCE: 13
gcatgcctgc agtaggcaat acggcacata                                  30

<210> SEQ ID NO 14
<211> LENGTH: 2297
<212> TYPE: DNA (genomic)
<213> ORGANISM: Nicotiana tabacum

<400> SEQUENCE: 14
ctagttatgg atgaggacag gttcattgaa gcttcaaatc tattcgatag tgggacctac    60
```

-continued

```
gtctcaaatc ccgaaaaaac tcgcgaaatc cgaacacccg ttccgctacg agttcaacca     120
tacaaaaatt atccaattct gatgtcaact cgaccctcaa atcttcaatt aaagtctttg     180
aagacttcta tcattttcaa ctcaatcttt atcccatttg aactaaacac tatttccata     240
aaaccttatt gatacgtata ataatactcc ttacacccaa gaattatact cttaatcacc     300
catcattacc caaactcgga attgaagatt aaaaccttac ctctttgatg aagaacttga     360
gggatttttt tgttggattt caaggcttgg acaagaattt gatgagcaag cactttatc      420 tacttcctct ctctagaaca ctctcacttc tctctaaaat catcagatag ttgccccaaa     480
acctatttat caaaatagag tcgggtaatg aaaataggta aatggaccct ccaaactcag     540
gtatgcgatt gcacaatgga tatacgggtc gcacaatgga ccaccaaatc gatgccgaaa     600
actgggttgc gctggacagg tctgcgaccc attttacggt cgcacaatgt gctacgaaga     660
ggaattcaca tagatttagg aagggcctgt tgtatttgtg tacaagctaa agttttttga     720
aaaacaaata cctttggtca cttcattgt caaataggtt tttccttcgt ataccttact      780
tacatcacat agtgattatg cgatcgcaca atttaccgca taatcgtatt tttccagctt     840
ttggtaattt aatcataact ttttttatga atatccaaat gacgaactgt ttgaagcgtt     900
agaaactaga ctcaaagatc tttcatttta taggcaatac ggcacataat attttgtatc     960
atgagagtta ttctcatttg aagttaggtc ttgtgtgaac tcacttgaaa ctttagtctt    1020
atgaaatttc caacttctac atccgattcc gaaacctatc gaatcaagtc cgattgacct    1080
caaattttgc atacaagcca taatgacat aacagagcta taaaattttt cgaaacggga     1140
ttccggctcc gatatcaaaa agtcaaccct gtggtcaaac ttggaaatct ttagccttta    1200
aattactagt ttccgttaaa tggtcataac ttgagttatg gacctccaaa ttaaattccg    1260
ggcatacgcc caagtcccat atcacgatac gaacctatag gaactttcaa atattgatc     1320 cggatccgtt tgctcaaaat gttgatcaaa gtcaactcag ttgagtttta aggctctagt    1380
tcacatttta atccattttc acctaaaaac tttccggaaa attttacgga tttcgcacgc    1440
aagtcgatga atgactttg gaggtcttag aacacgtaat taattattaa atttaaagat     1500
gacattttgg ataatcaccc aagtagtaca aatttttat gcggtgatta tatttgccaa     1560
tccatcaagc caaacatgtc gtaattagtc ataaattaag ttatacagga agaataatac    1620
gagaaatata atacctaaat taataaatac tactataaaa ttataatatt gatattgtgg    1680
ttgtattgcc catttcatta gaaggatat atgatgtata atataaaatt ttacaatgtt     1740
attcttgttt ttaaagttaa taaaaattta aaatatgaat ttaaggttat tcttgtttat    1800
agattcttta tatcataaag ctaatcctcg tataaattat ttcatattcg actcatataa    1860
actaatactg aaattactat ataagattat ataccggtat atattggaaa cgagacatca    1920
gccaaatgtg tccaaaaata ataaatatca aattttatat caggattatt ttttttgatt    1980
atgttaacaa agtaaaagt atcagactat aaatactgta gataagatca gccattatta    2040
gagataatac tctcactacc tatattgaaa gtgaagtaga cattttctga ggtggaatat    2100
ttaaaacgtt ttcagacatt taaaacctgg aatgcggagg caaagtagtg tagtacttac    2160
tagtagtata aataagtgat cccatttca aagtcaccgt caaaaatccc catttcaccg    2220
tttcctcgtt tctcctcctc actaattttg tctctttctc ttggtttgct attgtgctct    2280
tgtaggaatg cagtcgt                                                   2297
```

<210> SEQ ID NO 15
<211> LENGTH: 21
<212> TYPE: DNA (cDNA)

-continued

<213> ORGANISM: Nicotiana tabacum

<400> SEQUENCE: 15
catagccttg acttttggtg c                                      21

<210> SEQ ID NO 16
<211> LENGTH: 21
<212> TYPE: DNA (cDNA)
<213> ORGANISM: Nicotiana tabacum

<400> SEQUENCE: 16
cccaaattgt cgtgtctgaa g                                        21

<210> SEQ ID NO 17
<211> LENGTH: 21
<212> TYPE: DNA (cDNA)
<213> ORGANISM: Nicotiana tabacum

<400> SEQUENCE: 17
tctgagaaat ggaaccctga t                                        21

<210> SEQ ID NO 18
<211> LENGTH: 18
<212> TYPE: DNA (cDNA)
<213> ORGANISM: Nicotiana tabacum

<400> SEQUENCE: 18
ttcgagtctg ttgagcct                                          18

<210> SEQ ID NO 19
<211> LENGTH: 21
<212> TYPE: DNA (cDNA)
<213> ORGANISM: Nicotiana tabacum

<400> SEQUENCE: 19
ttcttccctc tcttgctggt t                                        21

<210> SEQ ID NO 20
<211> LENGTH: 21
<212> TYPE: DNA (cDNA)
<213> ORGANISM: Nicotiana tabacum

<400> SEQUENCE: 20
aggacgaaat gatgtaggaa a                                        21

<210> SEQ ID NO 21
<211> LENGTH: 23
<212> TYPE: DNA (cDNA)
<213> ORGANISM: Nicotiana tabacum

<400> SEQUENCE: 21
cgcattctat ctgttcctca tca                                      23

<210> SEQ ID NO 22
<211> LENGTH: 670
<212> TYPE: DNA (genomic)
<213> ORGANISM: Nicotiana tabacum
<220> FEATURE:
<221> NAME/KEY: unsure
<222> LOCATION: 415, 416, 417, 475

<400> SEQUENCE: 22
aggacgaaat gatgtaggaa aggtttatta ctgaccattc cagaattttt gcatcaccaa    60

-continued

```
gagctttaat atatatcttg ttcaatgagt ggcagagagc cttgcttggt aaaaaattag     120
aaatagaaat actaaaatta ttaactgctt ccttttttctg cccattttttt tcatgaaatg    180 ctaacataga gggtgtcatg cagcatgaat catctgcttc tgctacactc tttaacattc     240
tagccataca aaatgcaatg tccgtccccc ttattctttc ctgttagttg ttacctctct     300
tctatgacag tgtgagtatc ttctgttcca caatatactt caggtagagc ccttttcaac     360
tgtgatagaa cccctcggcg ttggttgttt catgtaaata caacaactga acttnnnggc     420
tgcctctttt tttgtttcct gaatatgttt tgacttgcac ttgaaaaata cattnggtta     480
cccaaatatt tccttttctt gctataggtg tcaaaacctg gctctgtgaa tgttgaaaag     540
ctcatgagcg tcgagcggta ttcccatgtg atgcacataa gctccacggc gagtccatat     600
tttgatttcg tccgaggtca tactggaatc taaattgcct tttgatgttc tttgttggct     660
ctaattttcc                                                            670
```

<210> SEQ ID NO 23
<211> LENGTH: 491
<212> TYPE: PRT
<213> ORGANISM: Nicotiana tabacum

<400> SEQUENCE: 23

```
Asp Asp Arg Glu Ala Pro Ser Phe Leu Phe Glu Ser Val Glu Pro Gly
  1               5                  10                  15

Ser Gln Met Ser Ser Val Gly Arg Tyr Ser Val Gly Ala Gln Pro
             20                  25                  30

Ala Met Glu Ile Val Ala Lys Glu Asn Lys Val Ile Val Met Asp His
         35                  40                  45

Asn Asn Glu Thr Met Ser Glu Glu Phe Val Glu Asp Pro Met Glu Ile
     50                  55                  60

Pro Arg Lys Ile Ser Glu Lys Trp Asn Pro Asp Pro Gln Leu Val Gln
 65                  70                  75                  80

Asp Leu Pro Asp Ala Phe Cys Gly Gly Trp Val Gly Phe Phe Ser Tyr
                 85                  90                  95

Asp Thr Val Arg Tyr Val Glu Lys Arg Lys Leu Pro Phe Ser Lys Ala
            100                 105                 110

Pro Glu Asp Asp Arg Asn Leu Pro Asp Met His Leu Gly Leu Tyr Asp
        115                 120                 125

Asp Val Val Phe Asp His Val Glu Lys Lys Ala Tyr Val Ile His
    130                 135                 140

Trp Ile Arg Leu Asp Gly Ser Leu Pro Tyr Glu Lys Ala Tyr Ser Asn
145                 150                 155                 160

Gly Met Gln His Leu Glu Asn Leu Val Ala Lys Leu His Asp Ile Glu
                165                 170                 175

Pro Pro Lys Leu Ala Ala Gly Asn Val Asn Leu Gln Thr Arg Gln Phe
            180                 185                 190

Gly Pro Ser Leu Asp Asn Ser Asn Val Thr Cys Glu Glu Tyr Lys Glu
        195                 200                 205

Ala Val Val Lys Ala Lys Glu His Ile Leu Ala Gly Asp Ile Phe Gln
    210                 215                 220

Ile Val Leu Ser Gln Arg Phe Glu Arg Arg Thr Phe Ala Asp Pro Phe
225                 230                 235                 240

Glu Val Tyr Arg Ala Leu Arg Val Val Asn Pro Ser Pro Tyr Met Gly
                245                 250                 255

Tyr Leu Gln Ala Arg Gly Cys Ile Leu Val Ala Ser Ser Pro Glu Ile
            260                 265                 270
```

```
Leu Thr Lys Val Lys Gln Asn Lys Ile Val Asn Arg Pro Leu Ala Gly
            275                 280                 285

Thr Ser Lys Arg Gly Lys Asn Glu Val Glu Asp Lys Arg Leu Glu Glu
        290                 295                 300

Leu Leu Glu Asn Glu Lys Gln Ser Ala Glu His Ile Met Leu Val Glu
305                 310                 315                 320

Leu Gly Arg Asn Asp Val Gly Lys Val Thr Lys Tyr Gly Ser Val Lys
                325                 330                 335

Val Glu Lys Leu Met Asn Ile Glu Arg Tyr Ser His Val Met His Ile
            340                 345                 350

Ser Ser Thr Val Thr Gly Glu Leu Gln Asp Gly Leu Thr Cys Trp Asp
        355                 360                 365

Val Leu Arg Ala Ala Leu Pro Val Gly Thr Val Ser Gly Ala Pro Lys
370                 375                 380

Val Lys Ala Met Glu Leu Ile Asp Glu Leu Glu Pro Thr Arg Arg Gly
385                 390                 395                 400

Pro Tyr Ser Gly Gly Phe Gly Gly Val Ser Phe Thr Gly Asp Met Asp
                405                 410                 415

Ile Ala Leu Ser Leu Arg Thr Ile Val Phe Pro Thr Ala Cys Gln Tyr
            420                 425                 430

Asn Thr Met Tyr Ser Tyr Lys Asp Ala Asn Lys Arg Arg Glu Trp Val
        435                 440                 445

Ala Tyr Leu Gln Ala Gly Ala Gly Val Val Ala Asp Ser Asp Pro Gln
    450                 455                 460

Asp Glu His Cys Glu Cys Gln Asn Lys Ala Ala Gly Leu Ala Arg Ala
465                 470                 475                 480

Ile Asp Leu Ala Glu Ser Ala Phe Val Lys Lys
            485                 490

<210> SEQ ID NO 24
<211> LENGTH: 1650
<212> TYPE: DNA (cDNA)
<213> ORGANISM: Nicotiana tabacum

<400> SEQUENCE: 24
ggatgaccgc gaagctccta gctttctttt cgagtccgtt gagcctggtt ctcagatgtc    60
tagcgttggt cgttatagcg ttgttggggc tcagcctgcg atggagatcg tggcaaagga   120
gaataaagtt attgtaatgg atcacaacaa tgaaaccatg tctgaggaat cgtcgaaga   180
tccaatggag atcccaagaa aaatctctga gaaatggaac cctgatcctc aactagttca   240
ggaccttcca gatgcgtttt gtggtgggtg ggttggtttt ttctcgtacg acactgttcg   300
ttatgttgag aagaggaaat tgccattttc aaaggcccct gaggatgata ggaacttgcc   360
agacatgcat cttggtctgt acgacgatgt agttgtattt gatcacgtgg aaaagaaagc   420
atatgtcatt cactggatta gactagatgg gagccttcct tacgaaaagg catacagtaa   480
tggaatgcaa catttggaga acttggtggc caagttacat gatattgagc cgccaaaact   540
ggctgcaggt aacgtgaatc ttcagacacg acaatttggg ccatctttgg ataattcaaa   600
cgtgacatgc gaagagtaca aggaggctgt ggtcaaggcc aaagaacata tacttgcagg   660
agacatattt cagatcgtgc tgagtcaacg ttttgagcgg cgaacatttg cagacccctt   720
tgaagtttat agagcactaa gagttgtgaa tccaagtccg tatatgggtt atttgcaggc   780
tagaggatgc atttggtag catcaagtcc agaaattctc accaaagtaa agcagaacaa   840
```

-continued

```
gatagtgaat cggccattgg caggaaccag caagagaggg aagaatgaag ttgaggataa       900
gagattagaa taggaactgc tagagaatga aaagcaaagt gctgagcaca tcatgttggt       960
tgaactcggt cgcaacgatg ttggaaaggt tacgaaatac ggatcagtga agtagagaa       1020 gcttatgaac atcgaacgtt attcccatgt tatgcatata agctccacgg tgacaggaga     1080
attacaagat ggtttgactt gctgggacgt actacgtgcg gctttaccag tgggaacagt     1140
tagtggtgca ccaaaggtca aagctatgga actaatcgat gagctagagc caacgaggcg     1200
tggaccatac agtggcggtt ttggtggagt ctccttcact ggtgacatgg acattgcttt     1260
atcccttagg acaatcgttt ttccgacagc atgtcaatac aatacaatgt actcttacaa     1320
ggatgctaac aaacggcgtg agtgggtggc ttatcttcaa gctggagctg gtgtagtagc     1380
tgatagtgac ccgcaagacg aacactgtga gtgccagaac aaagccgctg gtcttgctcg     1440
agccatcgac ttggctgaat ctgcatttgt gaaaaaatga ttgtgcccaa gaacagaggc     1500
tggctttctt tgaactccga gttcatgtgt ataaacagta caagcagaa acaaagtttt     1560 ttcttttttct tgattttgtg agaattgcaa ttagactcca ttaatgaagc tctgaaaaat     1620
gttacaatag aaaaaaaaaa aaaaaaaaaa                                      1650
```

<210> SEQ ID NO 25
<211> LENGTH: 2161
<212> TYPE: DNA (cDNA)
<213> ORGANISM: Nicotiana tabacum
<220> FEATURE:
<221> NAME/KEY: CDS
<222> LOCATION: LOCATION: 90..1940

<400> SEQUENCE: 25

```
gt caa aaa tcc cca ttt cac cgt ttc ctc gtt tct cct cct cac taa        47 ttt tgt ctc ttt ctc ttg gtt tgc tat tgt gct ctt gta gga atg cag        95
                                                            Met Gln tcg tta cct atc tca tac cgg ttg ttt ccg gcc acc cac cgg aaa gtt       143
Ser Leu Pro Ile Ser Tyr Arg Leu Phe Pro Ala Thr His Arg Lys Val
          5                  10                  15 ctg cca ttc gcc gtc att tct agc cgg agc tca act tct gca ctt gcg       191
Leu Pro Phe Ala Val Ile Ser Ser Arg Ser Ser Thr Ser Ala Leu Ala
     20                  25                  30 ctt cgt gtc cgt aca cta caa tgc cgc tgc ctt cac tct tca tct cta       239
Leu Arg Val Arg Thr Leu Gln Cys Arg Cys Leu His Ser Ser Ser Leu
 35                  40                  45 gtt atg gat gag gac agg ttc att gaa gct tct aaa agc ggg aac ttg       287
Val Met Asp Glu Asp Arg Phe Ile Glu Ala Ser Lys Ser Gly Asn Leu
 50                  55                  60 att ccg ctg cac aaa acc att ttt tct gat cat ctg act ccg gtg ctg       335
Ile Pro Leu His Lys Thr Ile Phe Ser Asp His Leu Thr Pro Val Leu
65                  70                  75                  80 gct tac cgg tgt ttg gtg aaa gaa gac gac cgt gaa gct cca agc ttt       383
Ala Tyr Arg Cys Leu Val Lys Glu Asp Asp Arg Glu Ala Pro Ser Phe
                 85                  90                  95 ctc ttt gaa tcc gtt gaa cct ggt ttt cga ggt tct agt gtt ggt cgc       431
Leu Phe Glu Ser Val Glu Pro Gly Phe Arg Gly Ser Ser Val Gly Arg
            100                 105                 110 tac agc gtg gtg ggg gct caa cca tct atg gaa att gtg gct aag gaa       479
Tyr Ser Val Val Gly Ala Gln Pro Ser Met Glu Ile Val Ala Lys Glu
        115                 120                 125 cac aat gtg act ata ttg gac cac cac act gga aaa ttg acc cag aag       527
His Asn Val Thr Ile Leu Asp His His Thr Gly Lys Leu Thr Gln Lys
    130                 135                 140
```

```
act gtc caa gat ccc atg acg att ccg agg agt att tct gag gga tgg      575
Thr Val Gln Asp Pro Met Thr Ile Pro Arg Ser Ile Ser Glu Gly Trp
145                 150                 155                 160 aag ccc aga ctc att gat gaa ctt cct gat acc ttt tgt ggt gga tgg      623
Lys Pro Arg Leu Ile Asp Glu Leu Pro Asp Thr Phe Cys Gly Gly Trp
                165                 170                 175 gtt ggt tat ttc tca tat gac aca gtt cgg tat gta gag aac agg aag      671
Val Gly Tyr Phe Ser Tyr Asp Thr Val Arg Tyr Val Glu Asn Arg Lys
            180                 185                 190 ttg cca ttc cta agg gct cca gag gat gac cgg aac ctt gca gat att      719
Leu Pro Phe Leu Arg Ala Pro Glu Asp Asp Arg Asn Leu Ala Asp Ile
        195                 200                 205 caa tta gga cta tac gaa gat gtc att gtg ttt gat cat gtt gag aag      767
Gln Leu Gly Leu Tyr Glu Asp Val Ile Val Phe Asp His Val Glu Lys
210                 215                 220                 225 aaa gca cat gtg att cac tgg gtg cag ttg gat cag tat tca tct ctt      815
Lys Ala His Val Ile His Trp Val Gln Leu Asp Gln Tyr Ser Ser Leu
                230                 235                 240 cct gag gca tat ctt gat ggg aag aaa cgc ttg gaa ata tta gtg tct      863
Pro Glu Ala Tyr Leu Asp Gly Lys Lys Arg Leu Glu Ile Leu Val Ser
            245                 250                 255 aga gta caa gga att gag tct cca agg tta tct ccc ggt tct gtg gat      911
Arg Val Gln Gly Ile Glu Ser Pro Arg Leu Ser Pro Gly Ser Val Asp
        260                 265                 270 ttc tgt act cat gct ttt gga cct tca tta acc aag gga aac atg aca      959
Phe Cys Thr His Ala Phe Gly Pro Ser Leu Thr Lys Gly Asn Met Thr
275                 280                 285 agt gag gag tac aag aat gct gtc tta caa gca aag gag cac att gct     1007
Ser Glu Glu Tyr Lys Asn Ala Val Leu Gln Ala Lys Glu His Ile Ala
                290                 295                 300                 305 gca gga gac ata ttt caa atc gtt tta agt caa cgc ttt gag aga aga     1055
Ala Gly Asp Ile Phe Gln Ile Val Leu Ser Gln Arg Phe Glu Arg Arg
            310                 315                 320 aca ttt gct gac cca ttt gaa gtg tac aga gca tta aga att gtg aat     1103
Thr Phe Ala Asp Pro Phe Glu Val Tyr Arg Ala Leu Arg Ile Val Asn
        325                 330                 335 cca agc cca tat atg act tac ata caa gcc aga ggc tgt att tta gtt     1151
Pro Ser Pro Tyr Met Thr Tyr Ile Gln Ala Arg Gly Cys Ile Leu Val
    340                 345                 350 gca tcg agc cca gaa att ttg aca cgt gtg aag aag aga aga att gtt     1199
Ala Ser Ser Pro Glu Ile Leu Thr Arg Val Lys Lys Arg Arg Ile Val
355                 360                 365 aat cga cca ctg gct ggg aca agc aga aga ggg aag aca cct gat gag     1247
Asn Arg Pro Leu Ala Gly Thr Ser Arg Arg Gly Lys Thr Pro Asp Glu
370                 375                 380                 385 gat gtg atg ttg gaa atg cag atg tta aaa gat gag aaa caa cgc gca     1295
Asp Val Met Leu Glu Met Gln Met Leu Lys Asp Glu Lys Gln Arg Ala
            390                 395                 400 gag cac atc atg ctg gtt gat tta gga cga aat gat gta gga aag gtg     1343
Glu His Ile Met Leu Val Asp Leu Gly Arg Asn Asp Val Gly Lys Val
        405                 410                 415 tca aaa cct ggt tct gtg aat gtc gaa aag ctc atg agc gtt gag cgg     1391
Ser Lys Pro Gly Ser Val Asn Val Glu Lys Leu Met Ser Val Glu Arg
    420                 425                 430 tat tcc cat gtg atg cac ata agc tcc acg gtc tct gga gag ttg ctt     1439
Tyr Ser His Val Met His Ile Ser Ser Thr Val Ser Gly Glu Leu Leu
435                 440                 445 gat cat tta acc tgt tgg gat gca cta cgt gct gca ttg cct gtt ggg     1487
Asp His Leu Thr Cys Trp Asp Ala Leu Arg Ala Ala Leu Pro Val Gly
450                 455                 460                 465
```

-continued

```
acc gtc agt gga gca cca aag gta aag gcc atg gag ttg att gat cag         1535
Thr Val Ser Gly Ala Pro Lys Val Lys Ala Met Glu Leu Ile Asp Gln
                470                 475                 480 cta gaa gta gct cgg aga ggg cct tac agt ggt ggg ttt gga ggc att         1583
Leu Glu Val Ala Arg Arg Gly Pro Tyr Ser Gly Gly Phe Gly Gly Ile
            485                 490                 495 tcc ttt tca ggt gac atg gac atc gca cta gct cta agg acg atg gta         1631
Ser Phe Ser Gly Asp Met Asp Ile Ala Leu Ala Leu Arg Thr Met Val
        500                 505                 510 ttc ctc aat gga gct cgt tat gac aca atg tat tca tat aca gat gcc         1679
Phe Leu Asn Gly Ala Arg Tyr Asp Thr Met Tyr Ser Tyr Thr Asp Ala
    515                 520                 525 agc aag cgt cag gaa tgg gtt gct cat ctc caa tcc ggg gct gga att         1727
Ser Lys Arg Gln Glu Trp Val Ala His Leu Gln Ser Gly Ala Gly Ile
530                 535                 540                 545 gtg gct gat agt aat cct gat gag gaa cag ata gaa tgc gag aat aaa         1775
Val Ala Asp Ser Asn Pro Asp Glu Glu Gln Ile Glu Cys Glu Asn Lys
                550                 555                 560 gta gcc ggt ctg tgc cga gcc att gac ttg gcc gag tca gct ttt gta         1823
Val Ala Gly Leu Cys Arg Ala Ile Asp Leu Ala Glu Ser Ala Phe Val
            565                 570                 575 aag gga aga cac aaa ccg tca gtc aag ata aat ggt tct gtg cca aat         1871
Lys Gly Arg His Lys Pro Ser Val Lys Ile Asn Gly Ser Val Pro Asn
        580                 585                 590 cta ttt tca agg gta caa cgt caa aca tct gtt atg tcg aag gac aga         1919
Leu Phe Ser Arg Val Gln Arg Gln Thr Ser Val Met Ser Lys Asp Arg
    595                 600                 605 gta cat gag aaa aga aac tag cga ata tga aga tgt aca taa att cta         1967
Val His Glu Lys Arg Asn
610                 615 aag tgg ttt tct tgt tca gtt taa tct ttt act gga ttg aga ctg tag         2015 ttg ctg aag ata gtt gtt tag aat gac ctt cat ttt ggt gtt cct gaa         2063 agg aca gtg cac ata tat agc aaa ttg atc aaa tgt tta atc ctt gta         2111 tgc ggg tga gaa tca atg cca tca gca att tgg aaa aaa aaa aaa aaa         2159 aa                                                                       2161
```

<210> SEQ ID NO 26
<211> LENGTH: 30
<212> TYPE: DNA (cDNA)
<213> ORGANISM: Nicotiana tabacum

<400> SEQUENCE: 26

```
    tgcgtacccg ggatgcagtc gttacctatc                                      30
```

<210> SEQ ID NO 27
<211> LENGTH: 31
<212> TYPE: DNA (cDNA)
<213> ORGANISM: Nicotiana tabacum

<400> SEQUENCE: 27

```
    gccggaattc tttccaaatt gctgatggca t                                    31
```

<210> SEQ ID NO 28
<211> LENGTH: 34
<212> TYPE: DNA (cDNA)
<213> ORGANISM: Nicotiana tabacum

<400> SEQUENCE: 28

```
           actagtggat cctgccttca ctcttcatct ctag                          34

<210> SEQ ID NO 29
<211> LENGTH: 42
<212> TYPE: DNA (cDNA)
<213> ORGANISM: Nicotiana tabacum

<400> SEQUENCE: 29
accttgagac ccgggttcaa cggattcaaa gagaaagctt gg                 42

<210> SEQ ID NO 30
<211> LENGTH: 42
<212> TYPE: DNA (cDNA)
<213> ORGANISM: Nicotiana tabacum

<400> SEQUENCE: 30
tccgttgaac ccgggtctca aggttctagt gttggtcgct ac                 42

<210> SEQ ID NO 31
<211> LENGTH: 33
<212> TYPE: DNA (cDNA)
<213> ORGANISM: Nicotiana tabacum

<400> SEQUENCE: 31
ttgcggggta ccctagtttc ttttctcatg tac                           33
```